United States Patent [19]
McEver et al.

[11] Patent Number: 5,605,821
[45] Date of Patent: Feb. 25, 1997

[54] EXPRESSION CONTROL SEQUENCES OF THE P-SELECTIN GENE

[75] Inventors: Rodger P. McEver; Junliang Pan, both of Oklahoma City, Okla.

[73] Assignee: Board of Regents of the University of Oklahoma, Norman, Okla.

[21] Appl. No.: 110,158

[22] Filed: Aug. 20, 1993

Related U.S. Application Data

[63] Continuation-in-part of Ser. No. 320,408, Mar. 8, 1989, Pat. No. 5,378,464.

[51] Int. Cl.$^6$ ............................. C12N 15/00; C07H 21/04
[52] U.S. Cl. ................... 435/172.3; 435/69.1; 435/320.1; 435/325; 435/366; 435/367; 435/371; 435/372; 435/365; 536/23.1; 536/23.5; 536/24.1; 536/24.31; 935/16; 935/23; 935/34
[58] Field of Search .................... 536/24.1, 23.5, 536/24.31, 23.1; 435/172.3, 69.1, 240.2, 320.1; 800/2; 935/6, 23, 34

[56] References Cited

U.S. PATENT DOCUMENTS

| | | | |
|---|---|---|---|
| 4,783,330 | 11/1988 | Furie et al. | 424/1.1 |
| 4,868,116 | 9/1989 | Morgan et al. | 435/240.2 |
| 4,980,286 | 12/1990 | Morgan et al. | 435/172.3 |
| 5,198,424 | 3/1993 | McEver | 514/13 |

FOREIGN PATENT DOCUMENTS

| | | |
|---|---|---|
| WO90/05786 | 5/1990 | WIPO. |
| WO91/07993 | 6/1991 | WIPO. |
| WO93/01286 | 1/1993 | WIPO. |

OTHER PUBLICATIONS

Takeda Chemical (1990) Gen Bank Accession No. Q03368.
Vallee et al (1991) Gen Bank Accession No. N71063.
Beutler et al (1993) Gen Bank Accession No. Q39286.
Whitsett et al (1991) Gen Bank Accession No. N80643.
Vansnick et al (1991) Gen Bank Accession No. Q12759.

FM Orson et al (1991) Nucleic Acids Research 19(12):3435–3441.
M Grigoriev et al (1992) J. Biol. Chem. 267(5):3389–3395.
Agrawal, S., et al., "Oligodeoxynucleoside Phosphoramidates and Phosphorothioates as Inhibitors of Human Immunodeficiency Virus", *Proc. Natl. Acad. Sci. USA*, 85:7079–7083 (1988).
Aruffo, A., et al., "CD62/P–Selectin Recognition Of Myeloid And Tumor Cell Sulfatides", *Cell*, 67: 35–44 (1991).
Aruffo, A., et al., "Granule Membrane Protein 140 (GMP140) Binds To Carcinomas And Carcinoma–Derived Cell Lines", *Proc. Natl. Acad. Sci. USA*, 89: 2292–2296 (1992).
Beckstead, J. H., et al., "Immunohistochemical Localization of Membrane and α–Granule Proteins in Human Megakaryocytes: Application to Plastic–Embedded Bone Marrow Biopsy Specimens", *Blood*, 67: 285–293 (1986).
Bevilacqua, M. P., et al., "Endothelial Leukocyte Adhesion Molecule 1: An Inducible Receptor for Neutrophils Related to Complement Regulatory Proteins and Lectins", *Science*, 243:1160–1165 (1989).
Bevilacqua, M. P., et al., "Identification of an Inducible Endothelial–leukocyte Adhesion Molecule", *Proc. Natl. Acad. Sci. USA*, 84:9238–9242 (1987).

(List continued on next page.)

*Primary Examiner*—Bruce R. Campell
*Attorney, Agent, or Firm*—Arnall Golden & Gregory

[57] ABSTRACT

DNA molecules and methods for the regulated expression of a gene in endothelial cells or megakaryocytes, are described, wherein the 5' flanking region of the P-selectin gene, or portions thereof, is ligated to the 5' end of a gene. The DNA molecules are also used as probes for screening individuals with abnormal levels of expression of P-selectin, or for production of pharmaceutical compositions to inhibit inflammation by inhibition of expression of P-selectin. These DNA molecules can also be used to identify and isolate previously unknown proteins which are involved in regulation of gene expression.

10 Claims, 7 Drawing Sheets

OTHER PUBLICATIONS

Bevilacqua, M. P., et al., "Inducible Endothelial Functions in Inflammation and Coagulation", *Seminars in Thrombosis and Hemostasis*, 13(4):425–433 (1987).

Bienvenu, K. and N. Granger, "Molecular Determinants Of Shear Rate–Dependent Leukocyte Adhesion In Postcapillary Venules", *Am. J. Physiol.*, 264 (*Heart Circ. Physiol.*, 33): H1504–H1508 (1993).

Blume, S. W., et al., "Triple Helix Formation by Purine–rich Oligonucleotides Targeted to the Human Dihydrofolate Reductase Promotor", *Nucleic Acids Research*, 20(7):1777–1784 (1992).

Bonfanti, R., et al., "PADGEM (GMP140) Is a Component of Weibel–Palade Bodies of Human Endothelial Cells", *Blood*, 73(5): 1109–1112 (1989).

Borman, S., "Glycotechnology Drugs Begin To Emerge From The Lab", *Chem. Eng. News*, pp. 27–34 (Jun. 28, 1993).

Bowen, B. R., et al., "Characterization of a Human Homologue of the Murine Peripheral Lumph Node Homing Receptor", *J. Cell Biol.*, 109:421–427 (1989).

Brandley, B. K., et al., "Carbohydrate Ligands of the LEC Cell Adhesion Molecules", *Cell*, 63:861–863 (1990).

Buttrum, S. M., et al., "Selectin–Mediated Rolling of Neutrophils On Immobilized Platelets", *Blood*, 82: 1165–1174 (1993).

Chomczynski, P., et al., "Single–step method of RNA Isolation by Acid Guanidinium Thiocyanate–Phenol–Chloroform Extraction", *Analytical Biochemistry*, 162:156–159 (1987).

Cooney, M., et al., "Site–specific Oligonucleotide Binding Represses Transcription of the Human c–myc Gene In Vitro", *Science*, 241:456–459 (1988).

Correl, L., et al., "Requirement For Sialic Acid On Neutrophils In A GMP–140 (PADGEM) Mediated Adhesive Interaction With Activated Platelets", *Biochem. Biophys. Res. Comm.*, 172(3): 1349–1356 (1990).

Crooke, S. T., "Progress Toward Oligonucleotide Therapeutics: Pharma Codynamic Properties", *The FASEB Journal*, 7(6):533–539 (1993).

Doré, M., et al., "P–Selectin Mediates Spontaneous Leukocyte Rolling in Vivo", *Blood*, 82: 1308–1316 (1993).

Dunlop, L. C., et al., "Characterization of GMP–140 (P–Selectin) As A Circulating Plasma Protein", *J. Exp. Med.*, 175: 1147–1150 (1992).

Duval–Valentin, et al., "Specific Inhibition of Transcription by Triple Helix–forming Oligonucleotides", *Proc. Natl. Acad. Sci.*, 89:504–508 (1992).

Gamble, J. R., et al., "Prevention of Activated Neutrophil Adhesion to Endothelium by Soluble Adhesion Protein GMP140", *Science*, 249: 414–417 (1990).

Geng, J.-G., et al., "Lectin Domain Peptides From Selectins Interact With Both Cell Surface Ligands and $Ca^{2+}$ Ions", *J. Biol. Chem.*, 267: 19846–19853 (1992).

Geng, J.-G., et al., "Rapid Neutrophil Adhesion To Activated Endothelium Mediated By GMP–140", *Nature*, 343: 757–760 (1990).

Goelz, S. E., et al., "ELFT: A Gene That Directs the Expression of an ELAM–1 Ligand", *Cell*, 63:1349–1356 (1990).

Grigoriev, M., et al., "A Triple Helix–forming Oligonucleotide–Intercalator Conjugate Acts as a Transcriptional Repressor Via Inhibition of $NH_k\beta$ Binding to Interleukin–2 Receptor α–Regulatory Sequence", *The Journal of Biological Chemistry*, 267(5):3389–3394 (1992).

Grober, J. S., et al., "Monocyte–Endothelial Adhesion In Chronic Rheumatoid Arthritis", *J. Clin. Invest.*, 91: 2609–2619 (1993).

Hamburger and McEver, "GMP–140 Mediates Adhesion of Stimulated Platelets to Neutrophils," *Blood*, 75: 550–554 (1990).

Handa, K., et al., "Selectin GMP–140 (CD62: PADGEM) Binds To Sialosyl–$Le^a$ And Sialosyl–$Le^x$, And Sulfated Glycans Modulate This Binding", *Biochem. Biophys. Res. Commun.*, 181: 1223–1230 (1991).

Hattori, R., et al., "Complement Protein C5b–9 Induce Secretion Of High Molecular Weight Multimers Of Endothelial Von Willebrand Factor And Translocation Of Granule Membrane Protein GMP–140 To The Cell Surface", *J. Biol. Chem.*, 264(15): 9053–9060 (1989).

Hattori, R., et al., "Stimulated Secretion Of Endothelial Von Willebrand Factor Is Accompanied By Rapid Redistribution To The Cell Surface Of The Intracellular Granule Membrane Protein GMP–140", *J. Biol. Chem.*, 264(14): 7768–7771 (1989).

Hattori, R., et al., "Complement C5b–9 Stimulates von Willebrand Factor Secretion from Human Endothelium", Abstracts of the 61st Scientific Sessions, Circulation Suppl. II, 78:II–117 (1988).

Hoff, S. D., et al., "Increased Expression Of Sialyl–Dimeric $Le^x$ Antigen In Liver Metastases Of Human Colorectal Carcinoma", *Cancer Res.*, 49: 6883–6888 (1989).

Hollenbaugh, D., et al., "Interaction of P–selectin (CD62) and Its Cellular Ligand: Analysis of Critical Residues", *Biochemistry*, 32(12):2960–2966 (1993).

Holt, J. T., et al., "An Oligomer Complementary to c–myc mRNA Inhibits Proliferation of HL–60 Promyelocytic Cells and Induces Differentiation", *Molecular and Cellular Biology*, 8(2):963–973 (1988).

Hourcade, D., et al., "The Regulators of Complement Activation (RCA) Gene Cluster", *Advances in Immunology*, 45:381–415.

Issekutz, A. C., et al., "Role of Neutrophils in the Deposition of Platelets During Acute Inflammation", *Laboratory Investigation*, 49(6):716724 (1983).

Itakura, K., et al., "Synthesis and Use of Synthetic Oligonucleotides", *Ann. Rev. Biochem.*, 53:323–357 (1984).

Johnston, et al., "Cloning Of GMP–140, A Granule Membrane Protein Of Platelets And Endothelium: Sequence Similarity To Proteins Involved In Cell Adhesion and Inflammation", *Cell*, 56: 1033–1044 (1989).

Johnston, et al., "Structure and Biosynthesis Of the Platelet α–Granule Membrane Protein, GMP–140", *Blood*, 70(5):, Suppl. 1: 352a Abstract No. 1264 (1987).

Johnston, G. I., et al., "Structure of Human Gene Encoding Granule Membrane Protein–140 of the Selectin Family of Adhesion Receptors for Leukocytes", *J. Biol. Chem.*, 265(34): 21381–21385 (1990).

Johnston, G. I., et al., "Cloning Of GMP–140: Chromosomal Localization, Molecular Heterogeneity And Identification Of cDNAs Predicting Both Membrane Bound And Soluble Proteins", *Blood*, 72, Suppl.: 327a, Abstract No. 1218 (1988).

Johnston, et al., "Structural And Biosynthetic Studies Of The Granule Membrane Protein, GMP–140, From Human Platelets And Endothelial Cells", *J. Biol. Chem.*, 264: 1816–1823 (1989).

Jungi, T. W., et al., "Platelet–Leukocyte Interaction: Selective Binding of Thrombin–Stimulated Platelets to Human Monocytes, Polymorphonuclear Leukocytes, and Related Cell Lines", *Blood*, 67(3):629–636 (1986).

Kijima–Suda, I., et al,. "Possible Mechanism Of Inhibition Of Experimental Pulmonary Metastasis of Mouse Colon Adenocarcinoma 26 Sublines By A Sialic Acid: Nucleoside Conjugate", *Cancer Res.*, 48: 3728–3732 (1988).

Kojima, N., et al., "Inhibition Of Selectin–Dependent Tumor Cell Adhesion To Endothelial Cells And Platelets by Blocking O–Glycosylation Of These Cells", *Biochem. Biophys. Res. Commun.*, 182: 1288–1295 (1992).

Larsen, et al., "PADGEM Protein: A Receptor That Mediates The Interaction Of Activated Platelets With Neutrophils And Monocytes", *Cell*, 59: 305–312 (1989).

Larsen, E., et al., "PADGEM–Dependent Adhesion Of Platelets To Monocytes And Neutrophils Is Mediated By A Lineage–Specific Carbohydrate, LNF III (CD15)", *Cell*, 63: 467–474 (1990) (GMP140 carbohydrate ligand).

Lasky, L. A., "Cloning of a Lymphocyte Homing Receptor Reveals a lectin Domain", *Cell*, 56:1045–1055 (1989).

Lawrence, M. B., et al., "Leukocytes Roll on a Selectin at Physiologic Flow Rates: Distinction from and Prerequisite for Adhesion Through Integrins", *Cell*, 65:1–20 (1991).

Levinovitz, A., et al., "Identification Of A Glycoprotein Ligands For E–Selectin On Mouse Myeloid Cells", *J. Cell Biol*, 121:449–459 (1993).

Ley, K., et al., "Lectin–Like Cell Adhesion Molecule 1 Mediates Leukocyte Rolling in Mesenteric Venules In Vivo", *Blood*, 2553–2555 (1991).

Liao, L., et al., "Oxidized Lipoproteins Elicit Leukocyte–Endothelial Cell Adhesion in Mesenteric Venules", *FASEB J., (Abstracts)*, 7: abstract No. 1986 (1993).

Lowe, J. B., et al., "A Transfected Human Fucosyltransferase cDNA Determines Biosynthesis Of Oligosaccharide Ligand(s) For Endothelial–Leukocyte Adhesion Molecule", *Biochem. Soc. Trans.*, 19: 649–653 (1991).

Lowe, J. B., et al., "ELAM–1–Dependent Cell Adhesion to Vascular Endothelium Determined by a Transfected Human Fucosyltransferase cDNA", *Cell*, 63:475–484 (1990).

Maher, III, L. J., et al., "Inhibition of DNA Binding Proteins by Oligonucleotide–directed Triple Helix Formation", *Science*, 245:725–730 (1989).

Mayadas, T. N., et al., "Leukocyte Rolling And Extravasation Are Severely Compromised In P Selectin–Deficient Mice", *Cell*, 74: 541–554 (1993).

McEver, R. P., "Misguided Leukocyte Adhesion", *J. Clin. Invest.*, 91: 2340–2341 (1993).

McEver, et al., "The Platelet α–Granule Membrane Protein GMP–140 Is Also Synthesized By Human Vascular Endothelial Cells and Is Present In Blood Vessels of Diverse Tissues", *Blood*, 70(5) Suppl. 1: 355a, Abstract No. 1274 (1987).

McEver, R. P., "Selectins: Novel Receptors that Mediate Leukocyte Adhesion During Inflammation", *Thrombosis and Haemostasis, F. K. Schattauer Verlagsgesellschaft mbH (Stuttgart)*, 65(3):223–228 (1991).

McEver and Martin, "A Monoclonal Antibody to a Membrane Glycoprotein Binds Only to Activated Platelets", *J. Biol. Chem.*, 259: 9799–9804 (1984).

McEver, R. P., "Leukocyte–Endothelial Cell Interactions", *Curr. Opin. Cell Biol.*, 4: 840–849 (1992).

McEver, R. P., "GMP–140: A Receptor For Neotrophils And Monocytes On Activated Platelets And Endothelium", *J. Cell. Biochem.*, 45: 156–161 (1991).

McEver, R. P. et al., "Properties of GMP–140, An Inducible Granule Membrane Protein Of Platelets And Endothelium", *Blood Cells*, 16: 73–83 (1990).

McEver, R., et al., "GMP–140, A Platelet α–Granule Membrane Protein, Is Also Synthesized By Vascular Endothelial Cells And Is Localized In Weibel–Palade Bodies", *J. Clin. Invest.*, 84: 92–99 (1989).

Mileski, W. J., et al., "Inhibition of CD18–dependent Neutrophil Adherence Reduces Organ Injury After Hemorrhagic Shock in Primates", *Surgery*, 206–212 (1990).

Mileski, W. J., et al., "Transient Inhibition of Neutrophil Adherence with the Anti–CD18 Monoclonal Antibody 60.3 does not Increase Mortality Rates in Abdominal Sepsis", *Surgery*, 497–501 (1991).

Moore, K. L. and L. F. Thompson, "P–Selectin (CD62) Binds To Subpopulations Of Human Memory T Lymphocytes And Natural Killer Cells", *Biochem. Biophys. Res. Commun.*, 186: 173–181 (1992).

Moore, K. L., et al., "GMP–140 Binds To A Glycoprotein Receptor On Human Neutrophils: Evidence For A Lectin–like Interaction", *J. Cell Biol.*, 112: 491–499 (1991).

Moore, K. L., et al., "Identification Of A Specific Glycoprotein Ligand For P–Selectin (CD62) On Myeloid Cells", *J. Cell Biol.*, 118: 445–456 (1992).

Müller–Eberhard, H. J., "Molecular Organization and Function of the Complement System", *Ann. Rev. Biochem.*, 57:321–347 (1988).

Mulligan, M. S., et al., "Protective Effects Of Oligosaccharides In P–Selectin–Dependent Lung Injury", *Nature*, 364: 149–151 (1993).

Mulligan, M. S., et al., "Neutrophil–Dependent Acute Lung Injury", *J. Clin. Invest.*, 90: 1600–1607 (1992).

Mulligan, R. C., "The Basic Science of Gene Therapy", *Science*, 260:929–932 (1993).

Narang, S. A., "Chemical Synthesis of Deoxyoligonucleotides by the Modified Triester Method", *Methods in Enzymology*, 65:610–621 (1980).

Nelson, R. M., et al., "Higher–Affinity Oligosaccharide Ligands For E–Selectin", *J. Clin. Invest.*, 91: 1157–1166 (1993).

Norgard, K. E., et al., "Characterization of a Specific Ligand for P–selectin on Myeloid Cells: A Minor Glycoprotein with Sialylated O–linked Oligosaccharides", *J. Biol. Chem.*, 268(17):12764–12774 (1993).

Offensperger, W–B., et al., "In Vivo Inhibition of Duck Lepatitis β Virus Replication and Gene Expression by Phosphorothioate Modified Antisense Oligodeoxynucleotides", *The EMBO Journal*, 12(3):1257–1262 (1993).

Ord, D. C., et al., "Structure of the Gene Encoding the Human Leukocyte Adhesion Molecule–1 (TQ1, Leu–8) of Lymphocytes and Neutrophils", *J. Biol. Chem.*, 265(14):7760–7767 (1990).

Orson, F. M., et al., "Oligonucleotide Inhibition of IL 2Rα mRNA Transcription by Promoter Region Collinear Triplex Formation in Lymphocytes", *Nucleic Acids Research*, 19(12):3435–3444 (1991).

Pan, J. and R. P. McEver, "Identification Of A Promoter Region In The Human GMP–140 Gene That Confers Tissue–Specific Expression", *Blood*, 78 (10) Suppl. 1: 279a, Abstract No. 1107 (1991).

Pan, J., et al., "Characterization of the Promoter for the Human P-selectin Gene", *J. Biol. Chem.*, 268:22600–22608 (1993).

Patel, K.D., et al., "Oxygen Radicals Induce Human Endothelial Cells To Express GMP-140 And Bind Neutrophils", *J. Cell Biol.*, 112(4): 749–759 (1991).

Phillips, M. L., et al., "ELAM-1 Mediates Cell Adhesion By Recognition Of A Carbohydrate Ligand, Sialyl-Le$^x$", *Science*, 250: 1130–1132 (1990).

Polley, M. J., et al., "CD62 And Endothelial Cell–Leukocyte Adhesion Molecule 1 (ELAM-1) Recognize The Same Carbohydrate Ligand, Sialyl-Lewis x", *Proc. Natl. Acad. Sci. USA*, 88: 6224–6228 (1991).

Postal, E. H., et al., "Evidence That a Triplex-forming Oligodeoxyribonucleotide Binds to the c-myc Promoter in HeLa Cells, Thereby Reducing c-myc mRNA Levels", *Proc. Natl. Acad. Sci.*, 88:8227–8321 (1991).

Rosen, S. D., "The LEC-CAMs: An Emerging Family of Cell–Cell Adhesion Receptors Based Upon Carbohydrate Recognition", *Am. J. Respir. Cell Mol. Biol.*, 3:397–402 (1990).

Sanders, W. E., et al., "Molecular Cloning and Analysis of in vivo Expression of Murine P-selectin", *Blood*, 80(3):795–800 (1992).

Sarin, P., et al., "Inhibition of Acquired Immunodeficiency Syndrome Virus by Oligodeoxynucleoside Methylphosphonates":, *Proc. Natl. Acad. Sci. USA*, 85:7448–7451 (1988).

Shaw, J., et al., "Modified Deoxyoligonucleotides Stable to Exonuclease Degradation in Serum", *Nucleic Acids Research*, 19(4):747.

Siegelman, M. H., et al., "Human Homologue of Mouse Lymph Node Homing Receptor: Evolutionary Conservation at Tandem Cell Interaction Domains", *Proc. Natl. Acad. Sci. USA*, 86:5562–5566 (1989).

Siegelman, M. H., et al., "Mouse Lymph Node Homing Receptor cDNA Clone Encodes a Glycoprotein Revealing Tandem Interaction Domains", *Research Articles*, 1165–1172 (1989).

Simpson, P. J., et al., "Reduction of Experimental Canine Myorcardial Reperfusion Injury by a Monoclonal Antibody (Anti-Mo1, Anti-CD11b) That Inhibits Leukocyte Adhesion", *J. Clin. Invest.*, 624–629 (1988).

Skinner, M. P., et al., "GMP-140 Binding To Neutrophils Is Inhibited By Sulfated Glycans", *J. Biol. Chem.*, 266: 5371–5374 (1991).

Skinner, M. P., et al., "Characterization Of Human Platelet GMP-140 As A Heparin–Binding Protein", *Biochem. Biophys. Res. Comm.*, 164: 1373–1379 (1989).

Springer, T. A., et al., "Sticky Sugars for Selectins", *Nature*, 349:196–197 (1991).

Stenberg, P., et al., "A Platelet Alpha–Granule Membrane Protein (GMP-140) Is Expressed on the Plasma Membrane after Activation", *J. Cell. Biol.*, 101: 880–886 (1985).

Stone, J. P. and Wagner, D. D., "P-Selectin Mediates Adhesion of Platelets To Neuroblastoma And Small Cell Lung Cancer", *J. Clin. Invest.*, 92: 804–813 (1993).

Szostak, J. W., "In Vitro Genetics", *Trends in Biochemical Sciences*, 17:89–93 (1992).

Takagi, K., et al., "Dissociation Kinetics of 19 Base Paried Oligonucleotide–DNA Duplexes Containing Different Single Mismatched Base Pairs", *Nucleic Acids Research*, 15(2):797–811 (1987).

Tedder, T. F., et al., "Isolation and Chromosomal Localization of cDNAs Encoding a Novel Human Lymphocyte Cell Surface Molecule, LAM-1", *J. Exp. Med.*, 170:123–133 (1989).

Tiemeyer, M., et al., "Carbohydrate Ligands for Endothelial–leukocyte Adhesion Molecule 1", *Proc. Natl. Acad. Sci. USA*, 88:1138–1142 (1991).

Todderud, G., et al., "Soluble GMP-140 Inhibits Neutrophil Accumulation In Induced Murine Peritonitis", *FASEB J.*, 6 (Abstracts Part I): abstract No. 5513 (1992).

Tuomanen, E. I., et al., "Reduction of Inflammation, Tissue Damage, and Mortality in Bacterial Meningitis in Rabbits Treated with Monoclonal Antibodies Against Adhesion-–Promoting Receptors of Leukocytes", *J. Exp. Med.*, 170:959–968 (1989).

Vedder, N. B., et al., "A Monoclonal Antibody to the Adherence–promoting Leukocyte Glycoprotein, CD18, Reduces Organ Injury and Improves Survival from Hemorrhagic Shock and Resuscitation in Rabbits", *J. Clin. Invest.*, 81:939–944 (1988).

von Andrian, U. H., et al., "Two-step Model of Leukocyte–endothelial Cell Interaction in Inflammation: District Roles for LECAM-1 and the Leukocyte $\beta_2$ Integrins In Vivo", *Proc. Natl. Acad. Sci. USA*, 88:7538–7542 (1991).

Walz, G., et al., "Recognition By ELAM-1 of the Sialyl-Le$^x$ Determinant on Myeloid and Tumor Cells", *Science*, 250: 1132–1135 (1990).

Watson, M. L., et al., "Genomic Organization of the Selectin Family of Leukocyte Adhesion Molecules on Human and Mouse Chromosome 1", *J.Exp. Med.*, 172: 263–271 (1990).

Watson, S. R., et al., "Neutrophil Influx Into an Inflammatory Site Inhibited by a Soluble Homing Receptor–IgG Chimaera", *Nature*, 349:164–167 (1991).

Weyrich, A. S., et al., "In Vivo Neutralization Of P-Selectin Protects Feline Heart And Endothelium In Myocardial Ischemia And Reperfusion Injury", *J. Clin. Invest.*, 91: 2620–2629 (1993).

Wickstrom, E. L., et al., "Human Promyelocytic Leukemia HL-60 Cell Proliferation and c-myc Protein Expression are Inhibited by an Antisense Pentadecadeoxynucleotide Targeted Against c-myc mRNA", *Proc. Natl. Acad. Sci.*, 85:1028–1032 1988).

Winn, R. K., et al., "Monoclonal Antibodies to P-Selectin Are Effective In Preventing Reperfusion Injury To Rabbit Ears", *Circulation (Suppl. I)*, 86, I-80 (abstract No. 316) (1992).

Winn, R. K., et al., "Anti-P-Selectin Monoclonal Antibody Attenuates Reperfusion Injury To The Rabbit Ear", *J. Clin. Invest.*, 92: 2042–2047 (1993).

Young, S. L., et al., "Triple Helix Formation Inhibits Transcription Elongation In Vitro", *Proc. Natl. Acad. Sci. USA*, 88:10023–10026 (1991).

Zamecnik, P. C., et al., "Inhibition of Rous Sarcoma Virus Replication and Cell Transformation by a Specific Oligodeoxynucleotide", *Proc. Natl. Acad. Sci.*, 75(1):280–284 (1978).

Zamencnik, P. C., et al., "Inhibition of Replication and Expression of Human T-cell Lymphotropic Virus Type III in Cultured Cells by Exogenous Synthetic Oligonucleotides Complementary to Viral RNA", *Proc. Natl. Acad. Sci.*, 83:4143–4146 (1986).

Zhou, Q., et al., "The Selectin GMP-140 Binds To Sialylated, Fucosylated Lactosaminoglycans On Both Myeloid And Nonmyeloid Cells", *J. Cell Biol.*, 115: 557–564. (1991).

Zhu, N., et al., "Systemic Gene Expression After Intravenous DNA Delivery Into Adult Mice", *Science*, 261:209–211 (1993).

Zimmerman, G. A., et al., "Thrombin Stimulates Neutrophil Adherence by an Endothelial Cell–Dependent Mechanism: Characterization of the Response and Relationship to Platelet–Activating Factor Synthesis", *Annals New York Academy of Sciences*, 485:349–368 (1986).

A Lauenu et al (1994) Oncogene 9: 527–536.

Dorfman, David M., et al., "Human Transcription Factor GATA-2." *J. of Biol. Chem.*, 267:1279–1285 (1992).

Paik, Young–Ki, et al., "Nucleotide sequence and structure of the human apolipoprotein E gene," *Proc. Natl. Acad. Sci., USA* 82:3445–3449 (1985).

R. E. Breitbart et al (1986) J Mol Biol 188: 313–324.

L. van de Zande et al (1990) Gene 87: 225–232.

J. A. Zwiebel et al (1989) Science 243: 220–222.

```
1362  GTCTGTCAAGCTTTGCAGTGCCAGGATCTCCAGTTGCCTTTAGTAGACAGTCAGTCTGCAGCTTGACCTGCAATGAAGGC      440
      V Q Q A L Q Q Q D L P V P N E A R V N ⊙ S M P P G A P R R Y Q S V Q S F T ⊙ N E ● G
1482  TTGCTCCTGTGGGAGCCAAGTGTCACACTTGCTTGCACACTTTGTTCTCCAGAATCTGTTCCTCCAGAATGGAACAATG      480
      L L V G A S V L Q ⊙ L A T G N W N S V P P E ⊙ Q A I P ⊙ T P L L S P Q ● N G T H ●
1602  ACCTGTGTTCAACCTCTTGGAAGTTCCAGTTATAAATCCACATGTCAATTCATCTGTCAGGAAAGATTGGATTGTACTGACGCTCTGACA      520
      T ⊙ V Q P P L G S S S Y K S T ⊙ Q F I ⊙ D E G Y S L S G P E R L D ⊙ T R S G R W T
                                    AGMPE2,E3,E4
1722  GACTCCCCACCAATGTGAAGGCCATCAAGTGCCCAGAACTCTTTGCCCCAGAGCAGGGCAGCCTGGATGTCTGACACCTCTGACACTCGTCTCATTTCTCT      560
      D S P P H ⊙ E A T K ⊙ P E L F A P E Q G S L D ⊙ S D T R G E F N V G S T ⊙ M F S
                                                              AGMPE2 E3 E4
1842  TGTAACAATGGCTTTAAGCTGGAGGGCCCCAATAATGTGGAAGATGGGAACTTCTGGAAGATGCACACCTTGGAACCTGCCAAGGGATCATCACTCCTACTCCAGGGTTGCAA      600
      ⊙ N N G F K L E G P N N V E ⊙ T T S G R W S A T P P T ⊙ K G I A S L P T P G L Q
1962  TGTCCAGCCCTCACCACTCCTGGGCAGGAACCATGTACTGTAGGACATCATCCGGAGAACCTTGTTTACTTTGCTGCAAGCTGTCGATTCACACTCATAGGAGAC      640
      ⊙ P A L T T P G Q G T M Y ⊙ R H H P G T F G F N T T ⊙ Y F G ⊙ N A G F T L I G D
2082  AGCACTCTGAGCTGCAGACCTTCAGGAGCAGTCAATGGACAGCAGTAACTCCAGAGAGCTGTGAAATGCTCAGAACTACATCTAATAGCAGATACATGTTAATAAGCAAATGCTGCCACTCGTGCCAACCTGG      680
      S T L S ⊙ R P S G Q W T A V T P A ⊙ R A V K ⊙ S E L E V N K P I A M N ⊙ S N L W ●
2202  GGAAACTTCAGTTATGGATCAATCTGCTCTCTTTCCATTGTGACTTACTTTGGTGGACGGTGCCTCTGGCTTTGCTTAAGAAAGCGTTTCAGACAA      720
      G F F S Y G S I ⊙ S F H ⊙ L E G Q L L N G S A Q T A ⊙ Q Q E N G H W S T T V P T ⊙
                  AGMPE1,E4
2322  CAAGCAGGACCATTGACTATCCAGGAAGCCCTGACTTACTTCTGGTGAGCGGGTGGCTCTCGGCTTTGCTAAGAAACCGTTTCAGACAA      760
      Q A G P L T I Q E A L T Y F G G A V A S T I G L I M G G T L L A L L R K R F R Q
          AGMPE1,E4
2442  AAAGATGATGGGCAAATGCCCCTGAATCCTCACAGCCACCTAGGAACATATGGAGTTTTTACAAACGGTCCTTCCATAAACACCCCATGAATCAAAGAC      789
      K D D G K ⊙ P L N P H S H L G T Y G V P F T N A A F D P S P ●
                  AGMPE1
2562  ATGGAATTACCTTAGATTAGCTCTGTAACACAGCCTGTTGGACCCGCTCCAGGAGAGCAGGAGCAATGTTTCTGCAGTAGTCTGCTTGAACAAACAGACTGGAGCA
      AGMPE3
2682  CCACCTCTCTCTCCTGTAACACAGCCACACAGAAGCCACAAGAGGAGCAGCAAATGTTTCTGCAGTAGTCTGCTTGAACAAACAGACTGGAGCA
2802  TCTGACTCACAAGAAGACCAGACTGTGGAGAATAAAAATACCTCTTTATTTTTGATTGAAGAAGTTTTCTCCACTTTGTTGAAAGCAGGTGGCATCTCTAATTGAAGAATTCC
2922  TGTAGCATCTTCTGGAGTCTCCAGTGGTTGCTGTTGATGAGGCCTCTGGTTGCCTCTGCTCTGCCAGAGAGTTCCTGATGGCACGAGCTTCCAGAGAGCCAGAATCAAGC
3042  TAGAAGGCCACATGTCACCGTGACCTTCACCGTGGACACTTCAGTCCACCAGTCACTCCCCAAATGACCAGTCACTCCCCTCAAATGACCAGTCACTCCCCTCAAATGCCTAATTAAAAGAATTTTCCCAAAAAAAAAAAAAAA
3162  AAAAAAAAAAAAAAAAAAAAAAAAAAAAAAAAAAAAAAAAAAAAAAAAA                                    3217
      AGMPE4                                                          AGMPE2
```

```
    -175                                    -136
    CAACATTACTCTTGCATTATCAACATTCTAACTTCATGG    P-selectin GATA
    ------------------TTTAGA---------------                Mutant -344                                     -306
    CTTTAAATTGGAGCTTATATCATAATCCAAGGAAACCTT    Nonconsensus GGCCTGGCCTTATCTCCGGCTGC              Endothelin-1 GATA
```

EXPRESSION CONTROL SEQUENCES OF THE P-SELECTIN GENE

This is a continuation-in-part of U.S. Ser. No. 07/320,408, U.S. Pat. No. 5,378,464, entitled "Method for Modulation of Inflammatory Responses" filed Mar. 8, 1989 by Rodger P. McEver.

BACKGROUND OF THE INVENTION

This invention is generally in the field of compositions and methods for the treatment and prevention of inflammatory responses involving P-selectin (formerly, GMP-140 or PADGEM) binding reactions, particularly adhesive interactions between platelets, leukocytes, and endothelial cells.

The adherence of leukocytes to vascular surfaces is a critical component of the inflammatory response, and is part of a complex series of reactions involving the simultaneous and interrelated activation of the complement, coagulation, and immune systems. Leukocyte adherence to vascular endothelium is a key initial step in migration of leukocytes to tissues in response to microbial invasion. The initial rolling contacts of leukocytes with the endothelium are mediated by the selectins, a family of receptors that interact with cell-surface carbohydrate ligands (reviewed in McEver, *Curr. Opin Cell Biol.*, 4, pp 840–859 (1992); Lasky, *Science*, 258, pp. 964–969, (1992)). These transient adhesive interactions allow time for leukocytes to become activated by signaling molecules that are released from the endothelium or the underlying tissues. Upon activation, leukocytes functionally upregulate members of the integrin family of adhesion receptors. The integrins strengthen adhesion by binding to immunoglobulin-like counter-receptors on the endothelial cell (McEver, *Curr. Opin Cell Biol.*, 4, pp 840–859 (1992)). Adhesion and signaling molecules function cooperatively to regulate leukocyte recruitment during the inflammatory response.

Leukocytes also adhere to activated platelets, through interactions of P-selectin on the activated platelet surface with carbohydrate ligands on the leukocyte surface (McEver, in *Structure, Function, and Regulation of Molecules Involved in Leukocyte Adhesion*, pp 135–150 (Lipsky et al., eds., Springer-Verlag, New York, 1993)). Platelet-leukocyte interactions may serve as important links between the hemostatic and inflammatory responses to tissue injury.

The coagulation and inflammatory pathways are regulated in a coordinated fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes. For example, the Mac-1 receptor on leukocytes, a member of the CD11-CD18 group, mediates phagocytosis and serves as a receptor for the degradation product of complement C3bi, is involved in one pathway of adherence of leukocytes to endothelium, mediates granulocyte aggregation, and binds coagulation Factor X.

Proteins involved in the hemostatic and inflammatory pathways are of interest for diagnostic purposes and treatment of human disorders. An example is P-selectin, formerly known as GMP-140 (granule membrane protein 140) or PADGEM, an integral membrane glycoprotein with an apparent molecular weight of 140,000 as assessed by sodium dodecyl sulfate polyacrylamide gel electrophoresis (SDS-PAGE). P-selectin contains an N-terminal lectin-like domain, followed by an epidermal growth factor-like module, a series of consensus repeats related to those in complement-binding proteins, a transmembrane domain, and a cytoplasmic tail, as described in the parent application, U.S. Ser. No. 07/320,408, filed Mar. 8, 1989, the teachings of which are incorporated herein. P-selectin is a member of the selectin family of adhesion receptors that mediate leukocyte interactions with vascular endothelium or platelets (McEver, *Curr. Opin. Cell Biol.*, 4, pp. 840–849 (1992); Lasky, *Science*, 258, pp. 964–969 (1992); Bevilacqua and Nelson, *J. Clin. Invest.*, 91, pp. 379–387 (1993)). The human P-selectin gene spans over 50 kilobases (kb) and contains 17 exons, most of which encode structurally distinct domains (Johnston et al., *J. Biol. Chem.*, 265, pp. 21381–21385 (1990)).

P-selectin was first purified (as GMP-140) from human platelets by McEver and Martin, *J. Biol. Chem.*, 259, pp. 9799–9804 (1984). Monoclonal and polyclonal antibodies to P-selectin were also prepared, as reported by McEver and Martin (1984) and P. E. Stenberg, et al., *J. Cell Biol.*, 101, pp. 80–886 (1985). The protein is present in alpha granules of resting platelets but is rapidly redistributed to the plasma membrane following platelet activation, as reported by Stenberg, et al., (1985). The presence of P-selectin in endothelial cells and its biosynthesis by these cells was reported by McEver, et al., *Blood*, 70(5) Suppl. 1:355a, Abstract No. 1274 (1987). In endothelial cells, P-selectin is found in storage granules known as the Weibel-Palade bodies. When platelet or endothelial cells are activated by mediators such as thrombin, the membranes of the storage granules fuse with the plasma membrane, the soluble contents of the granules are released to the external environment, and membrane bound P-selectin is presented within seconds on the cell surface, where it mediates adhesion of neutrophils, monocytes, and subsets of lymphocytes (McEver, in *Structure, Function, and Regulation of Molecules Involved in Leukocyte Adhesion*, pp. 135–150 (Lipsky et al., eds., Springer-Verlag, New York, 1993)).

The expression of P-selectin, as observed by immunohistochemistry (McEver et al., *J. Clin. Invest.*, 84, pp. 92–99 (1989)) and Northern blot analysis (Johnston et al., *Cell*, 56, pp. 1033–1044 (1989)), is restricted to megakaryocytes and endothelial cells. Under certain circumstances, steady-state levels of mRNA and protein are increased by inflammatory mediators such as tumor necrosis factor and endotoxin (Sanders et al., *Blood*, 80, pp. 795–800 (1992); Weller et al., *J. Biol. Chem.*, 267, pp. 15176–15183 (1992); Hahne et al., *J. Cell Biol.*, 121, pp. 655–664 (1993)). Thus, an understanding of the molecular mechanisms that control transcription of the P-selectin gene may help clarify the mechanisms for gene expression in megakaryocytes and endothelial cells and for regulation of leukocyte adhesion in response to tissue injury.

The promoters of several genes whose expression is restricted to endothelial cells or megakaryocytes have been partially characterized (Lee et al., *J. Biol. Chem.*, 265, pp. 10446–10450 (1990); Wilson et al., *Mol. Cell Biol.*, 10, pp. 4854–4862 (1990); Ravid et al., *Mol. Cell Biol.*, 11, pp. 6116–6127 (1991); Romeo et al., *Nature*, 344, pp. 447–449 (1990); Uzan et al., *J. Biol. Chem.*, 266, pp. 8932–8939 (1991)). The GATA element, initially recognized in erythroid-specific promoters, plays an important role in expression of some of these genes (Wilson et al., (1990), Romeo et al., (1990)). However, this element is not sufficient to mediate tissue-specific expression, as expression of the GATA-binding proteins does not directly correlate with expression of the genes containing GATA elements (Yamamoto et al., *Genes & Dev.*, 4, pp. 1650–1662 (1990)). A functional ETS element has been identified in the megakaryocyte-specific gene for glycoprotein IIb (Prandini et al., *J. Biol. Chem.*, 267, pp. 10370–10374 (1992); Lemarchandel et al., *Mol. Cell. Biol.*, 13, pp. 668–676 (1993)), but this element is also found in genes expressed in other tissues (see e.g., Macleod et al., *Trends Biochem. Sci.*, 17, pp. 251–256 (1992)).

It is an object of the present invention to characterize and provide DNA and RNA sequences of the 5' flanking region of the human P-selectin gene and to provide methods of using these sequences to specifically express P-selectin and other genes in endothelial cells and megakaryocytes.

It is another object of this invention to provide nucleic acid probes for screening for individuals with abnormal levels of P-selectin.

It is a further object of this invention to provide compositions and methods including the DNA or RNA sequences of the 5' flanking region of the human P-selectin gene for inhibiting or regulating P-selectin expression to control the inflammatory and hemostatic processes involving endothelial or megakaryocytic cells.

SUMMARY OF THE INVENTION

The 5' flanking region of the P-selectin gene contains the regulatory sequences necessary for expression of P-selectin in endothelial and megakaryocytic cells. These regulatory sequences are demonstrated to be useful to specifically express other genes in endothelial and megakaryotic cells, both in vitro, e.g., in tissue culture, and in vivo, e.g., in transgenic animals. In addition, these regulatory sequences can be used as probes to screen for individuals with abnormal levels of P-selectin and to make pharmaceutical compositions for the regulation or inhibition of P-selection expression in individuals having or predisposed to inflammation. Furthermore, sequences of the 5' flanking region of the P-selectin gene can be used to identify and isolate previously unknown proteins which are involved in regulation of gene expression.

BRIEF DESCRIPTION OF THE DRAWINGS

FIGS. 1a and 1b are a schematic of the nucleotide (SEQ ID NO:3) and deduced amino acid (SEQ ID NO:4) sequence of endothelial cell P-selectin that was determined from a composite of four overlapping cDNAs: lambda GMPE1-lambda GMPE4. The relative positions of each of the cDNAs are shown by the solid arrows. The dotted arrows indicate regions found in some clones, but deleted in others. The numbering of the nucleotide sequence was arbitrarily started at the first base following the adapter oligonucleotide sequence of the most 5' clone. The translated amino acid sequence of the open reading frame is given in the single-letter code. The initiating methionine was assigned to the first in-frame ATG sequence that agreed with the consensus sequence for initiation of translation. The stop codon is shown by the asterisk. The thin underlines show the matching positions of amino acid sequences determined from the N-terminus and from 26 peptides of platelet P-selectin. The signal peptide corresponds to positions -41 to -1. The putative transmembrane domain is heavily underlined. The cysteine residues are circled and potential asparagine-linked glycosylation sites (NXS/T) are shown by the dark circles. Two potential polyadenylation signals in the 3' untranslated region are underlined and overlined.

Figures 8, 9:
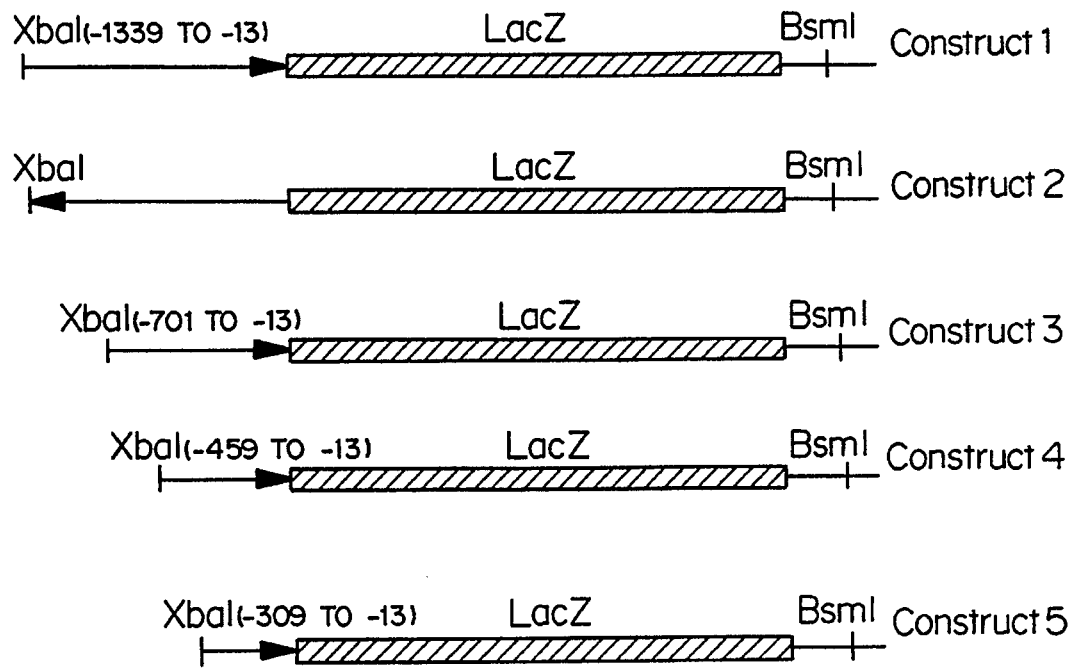
FIG. 8 demonstrates the binding of nuclear proteins to the regulatory sequence encompassing the GATA element. The sequences of the upper strand oligonucleotides were used as probes and competitors. The P-selectin GATA and the non-consensus GATA are from the indicated regions of the 5' flanking sequence of the human P-selectin gene. The mutant oligonucleotide contains three nucleotide changes in the core GATA motif of the wild-type P-selectin sequence; the same changes were used in the mutant expression constructs listed in FIG. 7. The endothelin-1 GATA oligonucleotide corresponds to the functional GATA element in the human endothelin-1 promoter (Wilson et al., *Mol. Cell. Biol.*, 10, pp. 4854–4862 (1990)).

FIG. 9 shows five different recombinant gene constructs used to make transgenic mice. Each construct contains a different portion of the 5' flanking region of the P-selectin gene fused to the lacZ gene. Arrows indicate the orientation of the portion of the 5' flanking region of the P-selectin gene fused to lacZ. Construct 2 is like Construct 1, except that the portion of the 5' flanking region of the P-selectin gene has been fused in the opposite orientation so that P-selectin gene promoter function is directed away from lacZ.

DETAILED DESCRIPTION OF THE INVENTION

I. Isolation, Cloning and Characterization of the Gene Encoding P-selectin and Regulatory Sequences Associated with the P-selectin Gene As used herein, unless otherwise specified, the term nucleic acid refers to DNA and the equivalent RNA.

Cloning of the gene for P-selectin was first reported by G. I. Johnston, R. G. Cook and R. P. McEver in Abstract 1238 Supplement II *Circulation*, 78(4) (October 1988). Oligonucleotides were prepared based on N-terminal amino acid sequencing of P-selectin peptides and used to screen a human endothelial cell cDNA library. A 3.0 Kilobase (kb) clone was isolated which encoded a protein of 727 amino acids. An N-terminal domain of 158 residues containing many cysteines, lysines, and tyrosines, is followed by an EGF-type repeating domain structure, and eight tandem repeats of 62 amino acids each, except for the sixth tandem repeat which has 70 amino acids. The repeats are homologous to those found in a family of proteins that include proteins regulating C3b and C4b, but are unique in having six conserved cysteines per repeat instead of the typical four. These are followed by a 24 amino acid transmembrane region and a 35 amino acid cytoplasmic tail.

As reported by Johnston, et al., in Abstract 1218, *Blood Suppl.* 72, 327a (November 1988), the gene for P-selectin has been localized to the long arm of chromosome 1, where genes for a number of C3b/C4b regulating proteins have been mapped.

As also reported, there appears to be at least two forms of the protein derived from alternative splicing of mRNA: a soluble form and a membrane or granule bound form. Both forms generally have a 186 bp insertion, encoding a ninth 62 amino acid tandem repeat, between the sixth and seventh tandem repeats of the sequence. The soluble protein has a deletion that removes 40 amino acids including the transmembrane region.

The conclusion that P-selectin serves as a receptor for the adherence of leukocytes to activated endothelial cells and platelets was based on several observations. First, the rapid appearance of P-selectin on the surface of endothelium stimulated with thrombin or histamine parallels the inducible adherence of neutrophils to endothelium stimulated with these agonists. In addition, platelets interact with neutrophils or monocytes only after activation with agonists such as thrombin which cause redistribution of P-selectin to the cell surface; platelet agonists such as ADP which do not induce degranulation and surface expression of P-selectin do not cause platelets to adhere to leukocytes. Second, in endothelium, P-selectin is concentrated in postcapillary venules, where E-selectin is concentrated. The concentration of both proteins in this region is important because postcapillary venules are the predominant sites for binding of leukocytes to platelets prior to their migration across the endothelium into the tissues. Third, purified P-selectin coated on tissue culture microtiter wells mediates specific adherence of purified neutrophils to the wells. Fourth, polyclonal and monoclonal antibodies to P-selectin block 60–90% of the adherence of neutrophils to cultured human umbilical vein endothelial cells stimulated with histamine. Fifth, the cDNA-derived amino acid sequence of P-selectin indicates that its structure is remarkably similar to that of E-selectin, an endothelial cell protein known to bind neutrophils. Sixth, leukocytes adhere to cells transfected with P-selectin cDNA.

The following methods were used for the production and characterization of P-selectin, antibodies thereto, and nucleotide sequences encoding P-selectin.

Protein Sequencing.

P-selectin was isolated and purified from human platelet membranes. On one occasion it was reduced under an atmosphere of nitrogen by the addition of dithiothreitol (20 mM, final concentration) and alkylated in the presence of iodoacetamide (Bray, et al., *Proc. Natl. Acad. Sci. USA*, 83, pp. 1480–1484 (1986). It was then digested with trypsin. The resultant peptides were isolated by two-step, reverse-phase, high performance liquid chromatography (HPLC) using previously described methods (Rosa, et al., *Blood*, 72:593–600 (1988). On a second occasion, P-selectin was reduced and alkylated in the presence of 50 µCi [$^{14}$C]-iodoacetamide (Amersham) before unlabeled iodoacetamide was added. It was then gel-purified (Bray, et al., 1986) and electroeluted into 25 mM Tris, 192 mM glycine, pH 8.0, containing 0.1% Triton X-100 (Jacobs and Clad, *Anal. Biochem.*, 154, pp. 583–589, 1986). One milligram of P-selectin was digested with endoglycosidase Glu-C (Boehringer-Mannheim Biochemicals) at a ratio of 1:10 w/w at 37° C. After 6 hr, an equal amount of protease was added and the mixture was incubated for a further 14 hr at 37° C. Peptides were isolated by reverse-phase HPLC as described by Rosa, et al., (1988), except that the initial separation on the C4 HPLC column was carried out using ammonium acetate buffer and the second separation on the C18 HPLC column was carried out using trifluoroacetic acid. Fractions containing the purified peptides were concentrated to 50 µl and kept frozen before sequencing. Amino acid sequences were determined from the N-terminus of the intact protein and from the peptides by using a gas-phase protein sequencer (Applied Biosystems Model 470A) (Rosa, et al., 1988). Cysteine residues were identified by their elution profile on the HPLC system used by the protein sequencer, and confirmed by measuring $^{14}$C radioactivity in duplicate aliquots from each sequencing cycle.

cDNA Screening.

Based upon a portion of the amino acid sequence data, two pools of a 35-mer oligonucleotide probe, designed according to codon usage tables (Lathe, *J. Mol. Biol.*, 183:1–12 (1985), were synthesized. The complementary strand was used to allow hybridization to RNA by Northern blotting. Inosine was used in one position because the third base of a glycine codon showed no preferential nucleotide. The sequences of the pools were:

POOL 1 (SEQ ID NO. 1):

5'-GC TGT CCA CTG ICC GAG GTT GTC ACA GCG CAC AAT-3'
                  A              A
                  C              T
                                 C

POOL 2 (SEQ ID NO. 2):

5'-GC TGT CCA CTG ICC GAG GTT GTC ACA TCT CAC AAT-3'
                  A            C
                  C

On Northern blots, both oligonucleotide probes hybridized to a 3.6 kb transcript from poly(A)$^+$ RNA isolated from CHRF-288 cells, a leukemia cell line with megakaryocyte-like properties (Witte, et al., *Cancer*, 58:238–244 (1986). Pool 2 probes hybridized more strongly and were therefore used to screen a cDNA library by standard procedures (Maniatis, et al., *Molecular Cloning: A Laboratory Manual* (Cold Spring Harbor Laboratory, Cold Spring Harbor, N.Y. 1982). Approximately 1.4 million recombinant phage from an unamplified human endothelial cell lambda gt11 library (Ye, et al., *J. Biol. Chem.*, 262, pp. 3718–3725 (1987) were plated out on *E. coli* Y1088 at a density of 200,000 plaques per 230-mm square plate of NZCYM agar. Duplicate nylon filters (Hybond-N, Amersham) were lifted, denatured, neutralized, and incubated at 42° C. for 24 hr in prehybridization solution containing 5× standard saline citrate (SSC) [1×SSC is 150 mM NaCl, 15 mM sodium citrate], 5×Denhardt's solution [0.02% Ficoll, 0.02% polyvinylpyrrolidone, 0.02% BSA], 0.2% SDS, and 200 µg/ml herring sperm DNA. The 35-mer oligonucleotide probe 2 was end-labeled with [gamma-$^{32}$P]ATP by 5'-polynucleotide kinase and was added to prehybridization solution to give a specific activity of 1×10$^6$ cpm/ml. The filters were hybridized at 42° C. overnight and the final washing conditions were 2×SSC, 0.1% SDS at 52° C. Positive plaques, identified by autoradiography of filters, were rescreened twice using the same probe and purified. The positive cDNA inserts were isolated from an agarose gel following digestion of phage DNA with SalI or EcoRI. Either enzyme could be used because, during the library construction, cDNAs were ligated to adapter oligonucleotides containing a SalI restriction site as well as an EcoRI site (Ye, et al., 1987). The inserts were subcloned into pIBI20 (IBI Biotechnologies, Inc.) for restriction mapping and DNA sequencing, and into M13mp18 (New England Biolabs) for DNA sequencing. Sequencing in M13mp18 was carried out by the dideoxy chain-termination procedure (Sanger, et al., *Proc. Natl. Acad. Sci. USA*, 74, pp. 5463–5467 (1977)) using either modified T7 polymerase (Sequenase from United States Biochemicals) or Klenow fragment of DNA polymerase (Bio-Rad Laboratories). Priming was performed with either the M13 universal primer or with 17-mer oligonucleotides designed from cDNA sequence. Double-stranded plasmid DNA, isolated by a standard alkaline-lysis mini-prep method (Maniatis, et al., 1982), was sequenced using the method described by Kraft, et al., *Biotechniques*, 6, pp. 544–547 (1988). The plasmid templates were primed with either universal primer, reverse primer (International Biotechnologies, Inc.), or 17-mer oligonucleotides.

Isolation and Characterization of cDNA Clones.

Three clones, positive after tertiary screening, were plaque purified, and phage DNA was prepared. The inserts from the clones, designated lambdaGMPE1, lambdaGMPE2, and lambdaGMPE3, were subcloned into plasmids and sequenced. The DNA sequences of all three clones contained long open reading frames which overlapped. The translated sequence of the longest clone, lambdaGMPE1, contained an amino acid sequence which matched the N-terminal amino acid sequence of intact platelet P-selectin but which lacked an in-frame ATG, which encodes a methionine to initiate translation, 5' to this sequence.

Figure 1A:
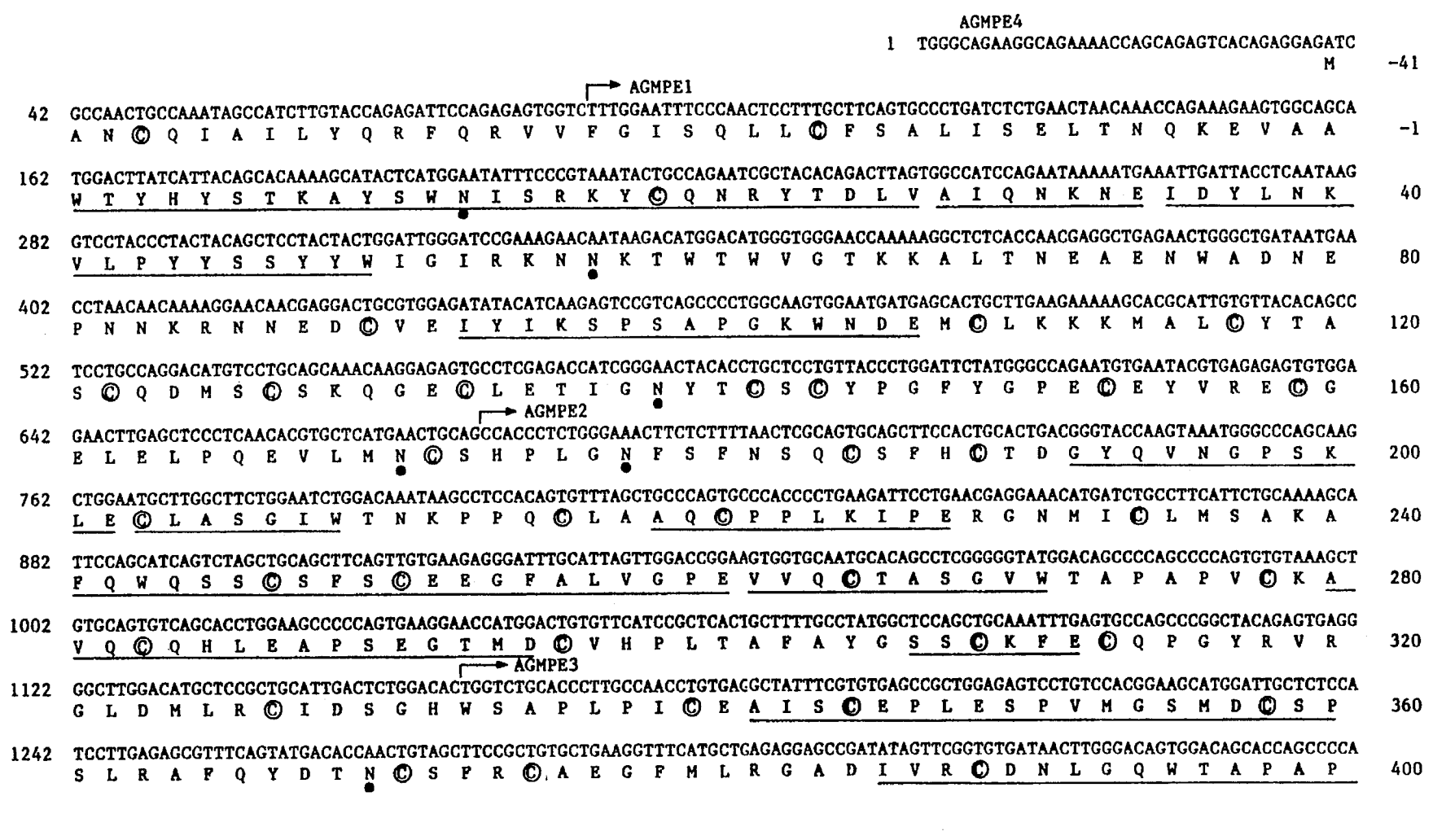

To identify full-length cDNAs, 1.4 million recombinant phage of the now amplified endothelial-cell cDNA library were rescreened with a 1 kb SmaI fragment from the 5' end of lambda GMPE1. Of the 55 positive clones indentified, five were purified. DNA sequence from the 5' end of one of these new clones, designated lambdaGMPE4, matched the 5' end of lambdaGMPE1, except that the first 88 bp were not found within the first 140 bp of lambdaGMPE1. Translation of the sequence of lambdaGMPE4 showed that there was an in-frame ATG sequence beginning at nucleotide 39. The sequence of the 5' end of lambdaGMPE4 was also found in the other four clones obtained in the second screening of the cDNA library, suggesting that it was the correct sequence and that the first 140 bp of lambdaGMPE1 was a cloning artifact. As shown in FIGS. 1a and 1b, sequence ID No.1 is a composite nucleotide sequence of the four clones, with 91% of the sequence derived from lambdaGMPE1. Sequence ID No. 2 is the predicted amino acid sequence.

The composite sequence predicts a 5' untranslated region of 38 bp, followed by an open reading frame of 2490 bp coding for a protein of 830 amino acids, then a 3' untranslated sequence of 614 bp including two potential polyadenylation signals of AATAAA and AATTAAA. The latter signal precedes a 12 bp sequence, then a poly(A)$^+$ tail of 75 bp. The nucleotide sequence GxxATGG, surrounding the first in-frame ATG beginning at base 39, agrees with the consensus sequence for initiation of protein translation (Kozak, *Nucl. Acids Res.*, 12, pp. 857–872 (1984)). Therefore the first amino acid was assigned to this codon.

When compared to the sequence of the other clones, there was a 186 bp segment deleted from lambda GMPE1, corresponding to nucleotides 1744 to 1929 (Sequence ID No. 1). A 120 bp deletion was also found in lambda GMPE2 and lambda GMPE3 (nucleotides 2326 to 2445). Eight single-base substitutions (confirmed by sequencing both strands of the cDNAs) were found in the first three clones. Three were silent substitutions, changing the third degenerate base of a codon. The other five produced conservative amino-acid changes.

Northern Blot Analysis.

Total RNA was prepared from the human megakaryocyte-like leukemia cell lines CHRF-288 (Witte, et al., *Cancer*, 58, pp. 238–244 (1986)) and HEL (Papayannopoulou, et al., *J. Clin. Invest.*, 79, pp. 859–866) (1982)), the myeloid cell line K562 (Lozzio and Lozzio, *Blood*, 45, pp. 321–334 (1975)), human umbilical vein endothelial cells, the EA.hy 926 hybrid endothelial cell line (Edgell, et al., *Proc. Natl. Acad. Sci. USA*, 80, pp. 3734–3737 (1983), human platelets, and the Daudi B-cell line (Klein, et al., *Cancer Res.*, 283, pp. 1300–1310 (1969)) by an acid-guanidinium-phenol-chloroform procedure (Chomczynski and Sacchi, *Anal. Biochem.*, 162:156–159 (1987)). Both HEL cells and K562 cells were treated with Phorbol myristate acetate (PMA) for 48 hr. to induce differentiation before RNA was prepared. Poly(A)$^+$ RNA was isolated from total RNA by oligo-dT cellulose chromatography (Davis, et al., *Basic Methods in Molecular Biology* (Elsevier, N.Y. 1986). Total or poly(A)$^+$ RNA was electrophoresed on a 1% agarose gel containing formaldehyde, then transferred to a Hybond-N nylon membrane by standard procedures (Maniatis, et al., *Molecular Cloning, A*

*Laboratory Manual* (Cold Spring Harbor, N.Y., 1982). The membrane was prehybridized in 5×SSC, 5×Denhardt's solution, 0.2% SDS, and 200 µg/ml herring sperm DNA for oligonucleotide probes, or in 5×Denhardt's solution, 50% formamide, 10% dextran sulfate, and 200 µg/ml herring sperm DNA for cDNA probes. Oligonucleotide probes were labeled by the procedure described above, and cDNA probes were random-labeled with a $\alpha$-$^{32}$P dCTP using the Klenow fragment of DNA polymerase in a commercial kit (Boehringer-Mannheim Biochemicals). Probes were hybridized overnight at 42° C. at a specific activity of at least $1\times10^6$ cpm/ml. The filters to which the oligonucleotides were hybridized were washed with 2×SSC, 0.5% SDS for 20-min periods at increasing temperatures up to 52° C., whereas those used with the cDNA probes were washed with 0.2× SSC, 0.1% SDS at temperatures up to 60° C. and were exposed to film (X-OMAT AR, Kodak) at –80° C. Molecular weight markers of lambda DNA (Boehringer-Mannheim Biochemicals), electrophoresed in parallel with the RNA samples, were visualized by including labeled lambda/HindIII DNA fragments (Bethesda Research Laboratories) [$5\times10^5$ cpm/ml] in the hybridization solution.

Southern Blot Analysis.

Human placental genomic DNA (intact or digested with EcoRI, BamHI, and BamHI/HindIII) were obtained from Oncor. Intact DNA was also digested with PstI, TaqI, and XbaI. Ten µg of each digested DNA was electrophoresed on a 1.5% agarose gel and transferred to a nylon membrane using a modification of the procedure of Reed and Mann, *Nucl. Acids Res.*, 13, pp. 7207–7221 (1985). Briefly, the gel was soaked in 0.2M HCl for 10 minutes, rinsed four times in water, and transferred to a nylon membrane in 0.4M NaOH buffer for 1 hr, then in 20×SSC overnight. The DNA was fixed to the membrane by exposure to UV light and hybridized with cDNA as described for the Northern blot. Lambda/HindIII fragments and ΦX174/HaeIII fragments (Bethesda Research Laboratories) were used as standards and were visualized by including randomly labeled DNA fragments of lambda and ΦX174 ($5\times10^5$ cpm/ml) in the hybridization solution.

Computer Analysis.

DNA and protein sequence were analyzed using the Genetics Computer Group software package of the University of Wisconsin (Devereux, et al., *Nucl. Acids Res.*, 12, pp. 387–395 (1984)). The amino acid sequence of P-selectin was compared with the published sequences of other proteins contained in the National Biomedical Research Foundation (NBRF) database (Release 16.0; 3/88).

The 5' Flanking Region of the Human P-selectin Gene

The following methods were used for the isolation and characterization of the 5' flanking region of the P-selectin gene.

Cells.

Human HL-60 promyelocytic cells (ATCC No. CCL240), K562 erythroid cells (ATCC No. CCL 243), HEL erythroleukemia cells (ATCC No. TIB180), and Jurkat T-lymphocytes were maintained in RPMI 1640 supplemented with 10% fetal calf serum (FCS). Human HeLa epithelioid cells (ATCC No. CCL 2), 293 human embryonal kidney cells (ATCC No. CRL 1573), and COS-7 SV40-transformed African green monkey kidney cells (ATCC No. CRL 1651) were maintained in Dulbecco's Minimal Essential Medium (DMEM, high glucose) supplemented with 10% FCS. CHRF-288 human megakaryocytic cells (Witte et al., *Cancer*, 58, pp. 251–256 (1986)) were maintained in Fisher's medium supplemented with 20% horse serum. Human umbilical vein endothelial cells (HUVEC) and bovine aortic endothelial cells (BAEC) were cultured as previously described (Moore et al., *J. Clin. Invest.*, 79, pp. 124–130 (1987)).

Genomic Cloning and Southern Blot Analysis.

A human genomic clone designated EMBL3-1 was obtained by screening a human genomic DNA library with a $^{32}$P-labeled P-selectin cDNA as described above and by Johnston et al., *J. Biol. Chem.*, 265, pp. 21381–21385 (1990). DNA restriction fragments derived from this clone were subcloned into the plasmid pIBI20 (IBI) for restriction enzyme mapping and DNA sequencing. All sequencing was carried out by the chain-termination procedure (Sanger et al., *Proc. Natl. Acad. Sci. USA*, 74, pp. 5463–5467 (1977)) using Sequenase (United States Biochemicals). Southern blot analysis of human placenta genomic DNA was done as previously described (Johnston et al., *Cell*, 56, pp. 1033–1044 (1989)) using a random-labeled probe corresponding to the 5' flanking region of the P-selectin gene from nucleotides (nt) 4405 to 4842 of SEQ ID NO. 5.

Determination of Transcriptional Start Sites.

Poly(A)$^+$ RNAs were prepared from cultured HUVEC, CHRF-288, HEL, and HL-60 cells by using the Fasttrack kit (Invitrogen). The poly(A)$^+$ RNAs were used for primer extension studies, RNase protection experiments, and anchored polymerase chain reaction (PCR) cloning. For primer extension analysis, a 27-mer primer was prepared with the sequence, 5'-TTCTGGTTTGTTAGTTCAGAGATCAGG-3'(SEQ ID NO. 6). The primer was 5' end-labeled with [$\gamma$-$^{32}$P]ATP (New England Nuclear, Inc) using T4 polynucleotide kinase (Pharmacia) and purified twice through a RNase free G-25 spin column (5'-3' Inc.). The specific activity of the labeled primer was $4\times10^6$ cpm/pmol. The annealing of the primer and the extension reaction were performed as described by Mackman et al., *Proc. Natl. Acad. Sci. USA*, 87, pp. 2254–2258 (1990) except that actinomycin D was not added. The reaction products were then extracted with phenol/chloroform, precipitated by ethanol, and separated on a 6% sequencing gel along with a known DNA sequencing ladder.

To confirm the results obtained by primer extension analysis, RNase protection studies were carried out with two different cRNA probes by the method of Cox et al., *Blood*, 77, pp. 286–293 (1991). Briefly, two genomic DNA fragments spanning the region from nt 4555 to 4842 and nt 4405 to 4842, respectively, of SEQ ID NO. 5 were amplified by PCR and subcloned into plasmid pIBI20 which contains a T7 promoter. The insert nucleotide sequences were confirmed. The recombinant plasmids were linearized with an appropriate restriction enzyme and the cRNA probes were generated with T7 RNA polymerase (Promega). The cRNA probes were then purified on a 6% sequencing gel. The linearized plasmids and cRNA probes were hybridized in 4M guanidine thiocyanate and 25 mM EDTA (pH 6.0) at 42° C. overnight, followed by treatment with RNase A and RNase T1 (Promega). Analysis of the protected products was performed as described for the primer extension studies.

As a definitive approach to determine the transcriptional start sites, anchored PCR (Frohman et al., *Proc. Natl. Acad. Sci. USA*, 85, pp. 8998–9002 (1988) was used to clone the 5' ends of a number of P-selectin cDNAs. First-strand cDNA was synthesized from 2 µg of HEL cell mRNA with the cDNA Cyclekit (Invitrogen), containing the strong RNA denaturant methylmercuric hydroxide (MeHgOH), with a specific primer, 5'-GATGTATATCTCCACGCAGTCCTCG-3' (SEQ ID NO. 7), which is complementary to nt 446–422 of SEQ ID NO. 3. After removing the excess primer with a Centricon 100 spin filter (Amicon), the 3' end of the first strand cDNA was tailed in a 30-µl volume containing tailing buffer (Bethesda Research Laboratories), 1 mM dATP, and 15 units of terminal deoxynucleotidyl-transferase (Bethesda Research laboratories) for 10 min at 37° C., and then heated for 15 min at 65° C. The reaction mixture was diluted to 200 µl, and 10-µl aliquots were used to synthesize the second strand cDNA with 10 pmol of the anchored-primer, 5'-GAATTCGAGCTCGGTACC TTTTTTTTTTTTTTTT-3'(SEQ ID NO. 8), using 2.5 units of Taq DNA polymerase (Cetus) at 72° C. for 7 min. The mixture was then subjected to PCR with two additional primers to improve specific amplification and facilitate subcloning: an adaptor primer, 5'-GAATTCG AGCTCGG-TACC-3'(SEQ ID NO. 9), which corresponded to the 5' end of the anchored primer and included restriction sites for EcoRI, SacI and KpnI, and a nested primer 5'-GTC-GACTCTAGAATCAGCCCAGTTCTCAGC-3' (SEQ ID NO. 10), which was complementary to nucleotides 378–395 of the cDNA sequence and included XbaI and SalI sites. PCR was performed in a Perkin-Elmer/Cetus thermal cycler; the amplification profile involved denaturation at 94° C. for 1.5 min, primer annealing at 55° C. for 2.5 min, and extension at 72° C. for 1 min. The anchored PCR products were detected by Southern blot analysis with two $^{32}$P-labeled internal oligonucleotides to verify the specificity of the reaction. The largest products were then subcloned into pIBI20, and plasmid inserts from 21 individual colonies were sequenced.

Construction of Chimeric Luciferase Expression Vectors.

Figure 2:
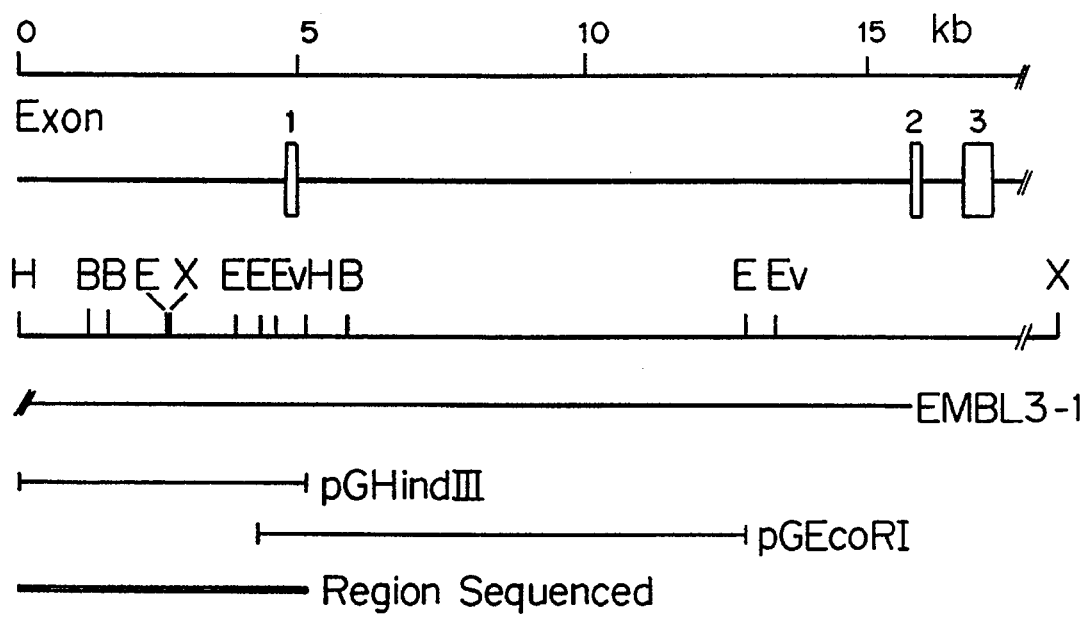
FIG. 2 is the structure of the 5' flanking region of the P-selectin gene. The map shows the cloned region (scale in kb) with the positions of exons (numbered 1–3) and the bacteriophage and plasmid clones used. The region of the 5' flanking region sequenced is shown by the open box. All restriction sites for the following enzymes are shown on the map: B=BamHI, E=EcoRI, Ev=EcoRV, H=HindIII, and X=XbaI.

Plasmid p0LUC (originally designated p19LUC) and pRSVLUC (DeWet et al., *Mol. Cell. Biol.*, 7, pp. 725–737 (1987)) were gifts from Dr. Donald Helinski (University of California, San Diego). The parental DNA for the creation of deletion mutants was a 5-kb HindIII fragment inserted into pIBI20 (pGHindIII, FIG. 2) that contained the 5' flanking region, first exon, and part of the first intron of the P-selectin gene. Plasmid p1339LUC in the correct orientation and p1339RLUC in reverse orientation were constructed by inserting the 1.3 kb P-selectin 5' flanking region excised by HinfI from pGHindIII into the SmaI site of p0LUC. Plasmids p701LUC, p701RLUC, p459LUC, p309LUC, p249LUC, p197LUC, p147LUC, p128LUC, p100LUC, and p80LUC were constructed by ligation of the respective DNA segments generated by PCR from pGHindIII into the SmaI site of p0LUC. Plasmid p4863LUC was constructed in three steps: 1) ligation into the EcoRV and EcoRI sites of pBluescript II KS (Stratagene, La Jolla, Calif.) of the fragment from nt 4596 to 4851 of SEQ ID NO. 5 released from p309LUC with EcoRV and EcoRI; 2) insertion between the HindIII and EcoRV sites of the above construct of a fragment from nt 1 to 4596 of SEQ ID NO. 5 released from pGHindIII with HindIII and EcoRV; and 3) removal by HindIII and SmaI of the sequence from nt 1 to 4851 of SEQ ID NO. 5 from the above construct followed by ligation into the HindIII and SmaI sites of p0LUC. Plasmid pm309LUC, pm249LUC, and pm197LUC, each of which contained three identical mutations in the TTATCA element, were constructed by an overlap extension PCR protocol (Disdier et al., *Mol. Biol. Cell*, 3, pp. 309–321 (1992)). Briefly, two separate PCR products, one for each half of the hybrid product, were generated with either an antisense or sense mutated GATA oligonucleotide (described below for the gel shift assay) and one outside primer. The two products were gel purified and mixed. A second PCR was then performed using the two outside primers. The PCR product was blunt-ligated into the SmaI site of p0LUC. All the constructs were verified by sequencing the inserts and flanking sites in the plasmid.

Molecular Cloning of the 5' Flanking Region of the P-selectin Gene.

The genomic clone EMBL3-1 encoding the 5' untranslated region of P-selectin cDNA was obtained, as described above, by screening a genomic DNA library with a $^{32}$P-labeled P-selectin cDNA (Johnston et al., *J. Biol. Chem.*, 265, pp. 21381–21385 (1990)). A 5 kb HindIII fragment encoding the 5-untranslated region of the P-selectin gene, derived from genomic clone EMBL3-1, was subcloned into pIBI20, analyzed by restriction mapping (FIG. 2), and sequenced on both strands. Southern blot analysis of human genomic DNA with a labeled DNA fragment derived from this clone revealed that restriction fragments were identical in size to those in the clone, suggesting that there was no DNA rearrangement during cloning.

Transcriptional Start Sites in the 5' Flanking Region.

Figure 3:
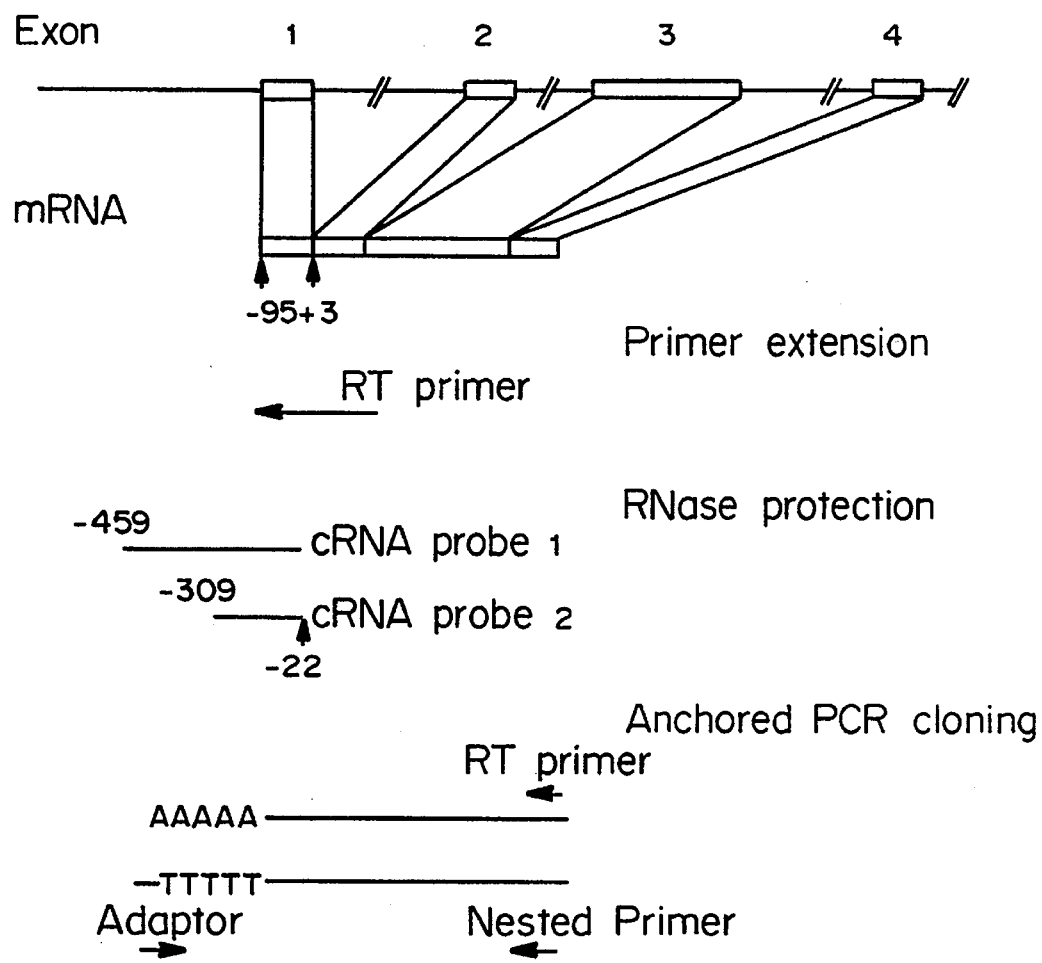
FIG. 3 illustrates the strategy to identify transcriptional start sites of the P-selectin gene and the primers used for primer extension studies and anchored polymerase chain reaction (PCR) and the probes used for RNase protection assays.

To define the transcriptional start sites for the P-selectin gene, three assays were used, as shown in FIG. 3.

To map transcriptional start sites by primer extension, 10 µg of poly (A$^+$) RNA from HEL cells, CHRF-288 cells, or HUVEC, or 10 µg of yeast tRNA was hybridized with a 5'-end-labeled oligonucleotide primer. After incubation with reverse transciptase, primer-extended products were analyzed on a 6% sequencing gel. A sequence ladder of the plasmid pIBI20 was used as size markers (lanes G, A, T, and C). At least 12 extension products were seen from nt 4769 to 4839 of SEQ ID NO. 5 relative to the ATG codon initiating translation of mRNA. Extension products of the same size were produced by mRNA from HUVEC and from the megakaryocytic cell lines CHRF-288 and HEL, but not by control tRNA.

Similar results were obtained by RNase protection assay using two independent cRNA probes surrounding the first exon. The two cRNA probes produced the same protected band patterns, most of which corresponded in size to the primer extension products. Ten micrograms of poly (A$^+$) RNA from HEL cells, HL-60 cells, or yeast tRNA were hybridized with each of the two different cRNA probes. After treatment with RNase, the protected products were run on a 6% sequencing gel. RNase-protected bands corresponding to the smallest primer extension products were not observed due to the short cRNA probes used. However, these short primer extension products were consistently observed, indicating that they reflected alternative transcriptional start sites rather than premature stops during reverse transcription.

To rule out generation of multiple bands through alternative splicing of pre-mRNAs, anchored PCR was performed to clone the 5' ends of cDNAs from HEL cell mRNA. Twenty-one clones were sequenced. The sequences of the 5' ends of these cDNA clones matched the genomic sequence and corresponded in length to those predicted from the primer extension and RNase protection products.

Figure 4:
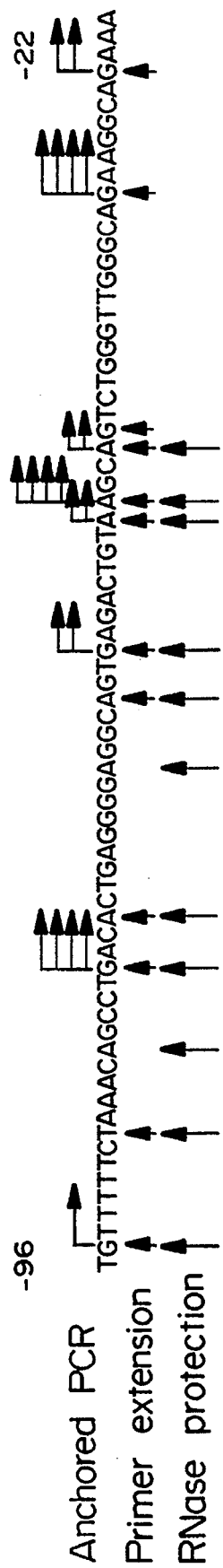
FIG. 4 shows a summary of transcriptional start sites in the 5' flanking region (Seq ID No:5) of the P-selectin gene. Vertical arrowheads, vertical arrows, and horizontal arrows indicate, respectively, the positions of the transcriptional start sites determined by primer extension, RNase protection and anchored-PCR cloning. Each horizontal arrow represents an independent cDNA clone obtained by anchored PCR with sequence beginning at the indicated position between nucleotides 4768 and 4842 of SEQ ID NO. 5.

The most abundant clones began at 4786, 4814, and 4832 (four clones each) of SEQ ID NO. 5, which matched the sizes of the most prominent products determined by RNase protection and/or primer extension. These data, summarized in FIG. 4, indicate that transcription of the P-selectin gene is initiated at multiple identical start sites in both endothelial and megakaryocytic cells.

Structural Features of the 5' Flanking Region.

The sequence of 4866 bp of 5' flanking region concluding with the ATG at the end of the exon 1 is shown in SEQ. ID NO:5. No canonical TATA and CCAAT boxes were found in the P-selectin flanking sequence. The nucleotide sequence was not GC rich and lacked a GC box (the binding site for transcription factor Sp1) that is found in many "housekeeping" genes without TATA boxes (Reynolds et al., *Cell*, 38, pp. 275–285 (1984)). It also lacked an "initiator" sequence which is required for accurate initiation of transcription in some TATA-less genes (Smale et al., *Cell*, 57, pp. 103–113 (1989)). A number of potential regulatory elements were present, including two sites at 4707–4711 and 4105–4110 recognized by the GATA family of zinc finger transcription factors (Yamamoto et al., *Genes & Dev.*, 4, pp. 1650–1662 (1990); Orkin, *Cell*, 63, pp. 665–672 (1990), a CACCC (GGGTG) element at 4648–4652 frequently seen in the promoters of erythroid-expressed genes (Frampton et al., *Mol. Cell. Biol.*, 10, pp. 3838–3842 (1990); Schule et al., *Nature*, 332, pp. 87–90 (1988), a GGGGGTGACCCC (4646–4657 of SEQ ID No. 5) overlapping with the CACCC element that is similar to the binding sites recognized by the subunit NFKB1 (p50) of the NF-κB/rel family (Blank et al., *Trends Biochem Sci.*, 17, pp. 135–140 (1992)) and by a zinc finger nuclear protein family that includes MBP-1 and MBP-2, 10 elements beginning at 4761, 4727, 4641, 4645, 4505, 4471, 4457, 4212, 4206, and 3732 of SEQ ID NO. 5, which contain a GGAAG/A SEQ core sequence that is similar to the binding site for the ETS class of oncoproteins (Karim et al., *Genes & Dev.*, 4, pp. 1451–1453 (1990)), and a TCTGGAATGTG (4747–4757 of SEQ ID NO. 5) that is related to the GT-IIC element of the SV40 enhancer (Burglin, *Cell*, 66, pp. 11–12 (1991)).

II. Cell Specific Expression Under the Control of the 5' P-Selectin Regulatory Sequence Transfection and Luciferase Assay.

Plasmids used for transfections were purified by cesium chloride banding. At least two different batches of plasmids for each construct were tested for the transfections. Cells were plated on a 100 mm petri dish at a density adjusted so that they reached 70–80% confluence prior to transfection. Equal volumes of 60 μg of test plasmid and 50 μg of lipofectin reagent (BRL), each diluted in 2.5 ml of Opti-MEM medium (BRL), were incubated for 20 min and the resulting transfection mixture was then added to the cells. After an 8 to 12 h incubation at 37° C., the transfection medium was replaced by complete medium for an additional 36 h and the cells were then harvested for luciferase assays in a total volume of 120 μl (DeWet et al., *Mol. Cell. Biol.*, 7, pp. 725–727 (1987)). Briefly, following lysis and removal of the cell debris by centrifugation, 20 μl of total cellular extracts were used for each measurement for luciferase activity. The luciferase activity for each transfection was measured three times with a Monolight 2001 luminometer. The luciferase activities were normalized to the amount of protein in cellular extracts as measured by the Bradford reagent (Bio-Rad).

Preparation of Cell Extracts and Gel Shift Assay.

HEL, CHRF-288, K562, Jurkat, Hela, and BAEC cell nuclear extracts were prepared as described by Dignam et al., *Nucl. Acids Res.*, 11, pp. 1475–1489 (1983). Extracts from HUVEC were prepared at miniscale as described by Schreiber et al., *Nucl. Acids Res.*, 17, pp. 6419 (1989). COS-7 cells were transfected with a plasmid encoding human GATA-2 (Dorfman et al., *J. Biol. Chem.*, 267, pp. 1279–1285 (1992)), a gift from Dr. Stuart Orkin (Harvard Medical School, Cambridge, Mass.), or mock-transfected with the plasmid pIBI20. Extracts from GATA-2-transfected or mock-transfected COS-7 cells were prepared as described in Tsai et al., *Nature*, 339, pp. 446–451 (1989). A standard gel shift assay (20 μl) contained 5,000–10,000 cpm of labeled oligonucleotide, 2.5 μg of poly(dI.dC), 60 mM KCl, 4 mM Tris (pH 7.5), 12 mM Hepes, 1 mM dithiothreitol, 1 mM EDTA, 10 μg bovine serum albumin, and 3 μl (6 μg) of cell extracts. Gels of 4–6% acrylamide (19:1 acrylamide/N, N'-methylenebis-acrylamide w:w) were run in 0.25×TBE buffer (1×TBE=0.089M Tris, 0.089M boric acid, and 0.002M EDTA) at 150 V and then dried prior to autoradiography. For competition experiments, unlabeled competitor duplex DNA was added to the reaction mixture before the addition of labeled probe.

Transgenic Mice.

The lacZ gene was excised from pCH110 (Pharmacia-LKB) by digestion with HindIII and ApaI and ligated into the phagemid, pBluescript SK+ (Stratagene), pre-digested with the same enzymes. Constructs 1–3 were prepared by removing the 5' flanking sequences of the P-selectin gene from, respectively, p1339LUC, p1339RLUC, and p701LUC (see above), by digestion with BamHI and XbaI and inserting the sequences into pBluescript at the corresponding sites such that the 5' flanking sequence was separated from lacZ by only a few base pairs of sequence in the polylinker region of the plasmid. Constructs 4 and 5 were prepared by excising the 5' flanking sequences from p459LUC and p309LUC with HindIII and EcoRI and inserting the sequences into the same lacZ-Bluescript vector.

Each of the five plasmids was purified on cesium chloride gradients. The insert containing the P-selectin 5' flanking region fused to lacZ was released from the plasmid by digestion with BamHI and XbaI. After purification from agarose gels, the DNA insert was microinjected into the pronuclei of oocytes obtained from mating mice. The microinjected oocytes were then implanted into the infundibulum of the Fallopian tubes of pseudopregnant mice using standard techniques (Hogan et al. in *Manipulating the Mouse Embryo. A Laboratory Manual*, Cold Spring Harbor Laboratory, Cold Spring Harbor, N.Y., 1986) (incorporated herein by reference). Incorporation of the transgene into offspring was determined by PCR analysis of tail-vein DNA, using primers specific for the 5' flanking sequence and the lacZ sequence (Chen and Evans, *Biotechniques*, 8, 32–33 (1990)). Expression of the transgene in tissues of founder mice or their offspring was determined by a cytochemical staining procedure for β-galactosidase (Sanes et al., *EMBO J.*, 5, pp. 3133–3142 (1986)).

Transient Expression Analysis of the 5' Flanking Region.

Figure 5:
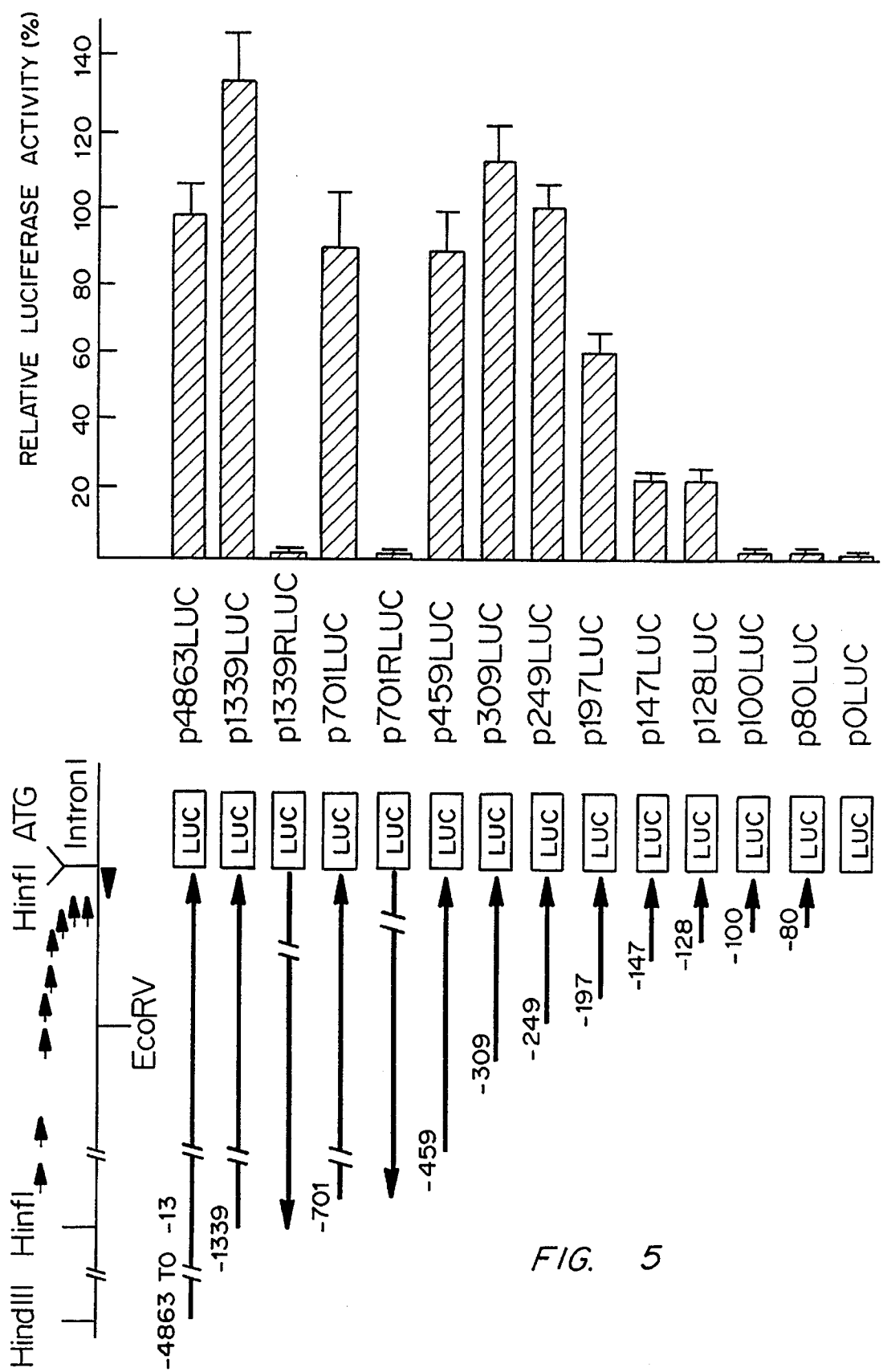
FIG. 5 demonstrates transient expression analysis of P-selectin gene promoter activity. On the left are diagrams of the P-selectin promoter-luciferase fusion constructs. Vertical bars indicate the restriction sites used to make the constructs. The PCR primers used to generate the shorter constructs are depicted with short arrows. The constructs are aligned with the 5' P-selectin gene sequences numbered relative to the translational start site. Constructs p1339RLUC and p701RLUC have 5' flanking sequence oriented in the reverse direction. On the right is plotted the relative luciferase activity of bovine aortic endothelial cells (BAEC) transfected with each construct. Activity is graphed as a percentage, with 100% equal to 24,000 light units per 25 µg of cellular protein. The data represent the means ±SD of at least three independent experiments. Duplicate transfections were performed in each experiment; the variation between duplicates did not exceed 10% of the mean for the experiment.

To test whether the 5' flanking region of the P-selectin gene had promoter activity, chimeric constructs were prepared in which serially deleted fragments of 5' flanking sequence were inserted before a promoterless luciferase gene in the plasmid pOLUC (FIG. 5). Luciferase expression was measured following transfection of the constructs into BAEC. Constructs p4863LUC, p1339LUC, p701LUC, p459LUC, p309LUC, and p249LUC promoted similar levels of luciferase activity that were significantly higher than the background amounts in pOLUC-transfected cells. Serial decreases in expression were observed following transfection with p197LUC and with p147LUC and p128LUC. Only background expression was observed following transfection with p100LUC and p80LUC. These data indicate that the sequences responsible for most of the promoter activity are located between 4615 and 4861 of SEQ ID NO. 5. These data also indicate that there are at least three positive regulatory domains between 4615 and 4764 of SEQ ID NO. 5 (e.g., compare p249LUC, p197LUC, p128LUC, and p100LUC). The results also show that some of the positive elements in the longer constructs were position dependent, as p1339RLUC and p701RLUC, which contained flanking sequence in reverse orientation, expressed no more luciferase in BAEC than p0LUC.

Figure 6:
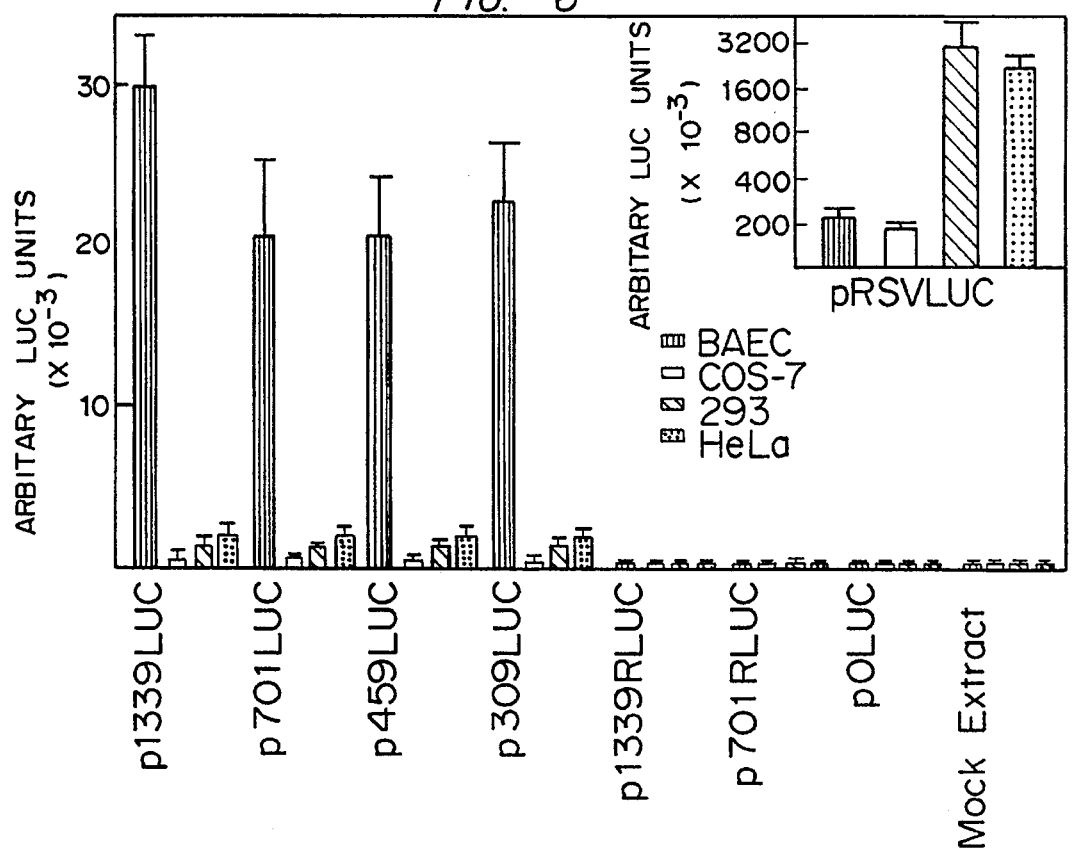
FIG. 6 demonstrates cell-specific expression of the 5' flanking sequence of the human P-selectin gene. The P-selectin-expressing BAEC and the P-selectin-nonexpressing cell lines HeLa, 293, and COS-7 were transfected with the indicated constructs. Parallel transfections with the positive control plasmid pRSVLUC were simultaneously performed. Luciferase activity is expressed as light units per 25 µg of cellular protein. The data represent the means ±SD of three independent experiments. Duplication transfections were performed in each experiment.

To determine whether the constructs mediated tissue-specific expression, they were transfected into COS-7, 293, and Hela cells, which do not normally synthesize P-selectin, as shown by FIG. 6. In contrast to their effects in BAEC, constructs p1339LUC, p701LUC, p459LUC, and p309LUC had only basal promoter activity in these cells, although the basal levels did exceed the background activity of mock-transfected cells or cells transfected with p0LUC. Parallel transfections with RSVLUC, a plasmid containing luciferase driven by the Rous sarcoma virus promoter, resulted in high levels of expression, indicating that the cells could be transfected. These data indicate that the flanking sequence from nt 4555 to 4851 of SEQ ID NO. 5 includes elements that can direct the regulated expression of a gene in endothelial cells.

The GATA Element at 4706 of SEQ ID NO. 5 is Required for Optimal Function of the P-selectin Promoter.

Deletion of the sequence between nt 4667 and 4717 of SEQ ID NO. 5 significantly reduced luciferase expression in BAEC, as shown by FIG. 5, indicating the presence of a positive regulatory element(s) in this region. To determine whether the GATA (TTATCA) element at 4706 of SEQ ID NO. 5 functioned as such a positive element, the wild-type sequence TTATCA was mutated to TTTAGA in the three constructs p309LUC, p249LUC, and p197LUC, as shown by FIG. 6. When the mutant constructs were transfected into BAEC, luciferase expression in each case was reduced to the level of p147LUC, which was only 20% of that produced by p309LUC. These results indicate that the GATA element is essential for optimal transcription of the P-selectin gene, perhaps through interactions with other regulatory sequences located between nt 4555 to 4666 of SEQ ID NO. 5.

Gene Expression in Megakaryocytes of Transgenic Mice Containing the P-selectin Promoter.

The use of the 5' flanking region of the P-selectin gene to direct the expression of a heterologous gene in megakaryocytes was demonstrated by analysis of transgenic mice carrying portions of the 5' flanking region of the P-selectin gene fused to the bacterial lacZ gene.

Five constructs were made in which DNA, having the sequence of nt 3525 to 4851 (or the same sequence inserted in the opposite orientation), 4163 to 4851, 4405 to 4851, or 4555 to 4851 of SEQ ID NO. 5, was fused to the 5' coding region of the lacZ gene, as described in FIG. 9. Each construct was then cloned and used to prepare transgenic mice as described above. Offspring carrying the transgenes for each of the five constructs were produced from founders. An analysis of bone marrow cells from mice carrying the construct having the sequence of nt 4163 to 4851 of SEQ ID NO. 5 fused to lacZ indicated that the transgene was expressed by megakaryocytes but not by other bone marrow cells.

The above results clearly indicate that the sequences of the 5' flanking region of the P-selectin gene can specifically direct the regulated expression of a gene in endothelial and megakaryocytic cells. Accordingly, a gene can be specifically expressed in endothelial cells or megakaryocytes by ligating, or otherwise fusing (e.g., by PCR), the 5' end of the coding sequence of the gene to the 3' end of a DNA sequence consisting essentially of nucleotides 1 to 4863 of SEQ ID NO. 5, or one or more of the transcriptional regulatory sequences of SEQ ID NO. 5, to yield a recombinant gene construct, and transfecting, or otherwise inserting using methods known to those skilled in the art (e.g., by transgenic methods, microinjection, liposome fusion) the recombinant gene construct into endothelial cells or megakaryocytes.

It is likely that some modifications in the sequence of the 5' flanking region can be introduced into the cells without alteration in function. For example, the 5' flanking sequences of a given gene in different species may be slightly different; the differences are usually in regions not critical for function and therefore not conserved among species. It is believed that the 5' flanking sequences of the P-selectin gene in other species will also be functional in humans; this prediction is supported by the observed function of the human P-selectin flanking sequence in transgenic mice (see above).

III. The 5'-P Selectin Regulatory Sequence can be used to isolate Novel Proteins The Function of the GATA Element Correlates with its ability to Bind Nuclear Proteins.

To determine whether the GATA element bound nuclear proteins, a 40-bp double-stranded oligonucleotide probe encompassing this sequence was synthesized, as shown in FIG. 8. The $^{32}$P-labeled probe was incubated with nuclear extracts from various cell lines in the presence of poly (dI.dC) as a competitor for nonspecific DNA-protein interactions. The resultant complexes were separated by electrophoresis on a nondenaturing polyacrylamide gel. For example, two distinct complexes (labeled A and B, where A has the slower mobility in the gel) were observed on gels when K562 and HEL cell nuclear extracts were incubated with end-labeled P-selectin GATA oligonucleotide. Complex formation was sequence specific, as it was prevented by addition of a 100-fold molar excess of the unlabeled GATA oligonucleotide, but not by a 100-fold excess of an oligonucleotide encoding a nonconsensus GATA sequence located further upstream in the P-selectin 5' flanking region. Similar complexes were formed using nuclear extracts from CHRF-288, BAEC, HUVEC, and Jurkat cells, although sometimes one of the complexes was only present in relatively small amounts. Two minor complexes were also observed in the gels, but these appeared to represent proteolytic degradation products as they were noted only in nuclear extracts stored for prolonged intervals.

To determine whether the GATA element was required to form the observed complexes in the gel shift assays, competition gel shift assays were carried out on HEL cell nuclear extracts with an oligonucleotide encoding the GATA motif from the human endothelin-1 gene promoter and the results compared to a competition gel shift assay carried out with the oligonucleotide encoding the P-selectin GATA motif, as shown by FIG. 8. The results indicated that the unlabeled human endothelin-1 GATA oligonucleotide probe prevented formation of complex B, but not complex A, by the $^{32}$P-labeled P-selectin probe containing the GATA consensus sequence. The labeled endothelin-1 probe formed a complex with a mobility similar, although not identical, to complex B. Formation of this complex was prevented by addition of either the unlabeled endothelin-1 probe or the P-selectin probe.

These data indicate that complex B represents the interaction of a member of the GATA protein family with the GATA consensus sequence in the P-selectin promoter.

Figure 7:
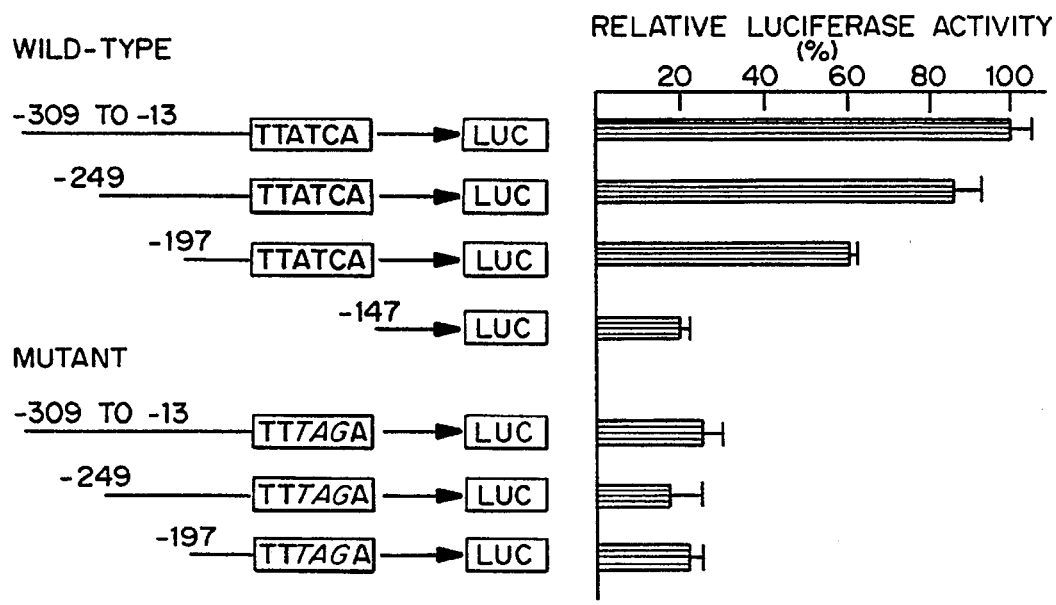
FIG. 7 is the mutational analysis of the GATA element. Three wild-type truncated chimeric constructs, and their three corresponding mutant constructs in which the TTATCA sequence was changed to TTTAGA, are depicted on the left of the figure. These constructs were transfected into BAEC, and the luciferase activities were measured as percent relative luciferase activity. The data represent the means ±SD of three independent experiments. Duplicate transfections were performed in each experiment; the variation between duplicates did not exceed 5% of the mean for the experiment.

To test whether the core GATA sequence was required for binding of nuclear proteins, a mutant oligonucleotide was synthesized (FIG. 8) in which the core sequence TTATCA was converted to TTTAGA, the same changes made in the mutant constructs shown in FIG. 7. HEL cell and BAEC nuclear extracts were incubated with end-labeled wild-type or mutant P-selectin GATA probe in the absence or the presence of the indicated unlabeled competitor. The results showed that a 100-fold molar excess of the unlabeled mutant probe prevented formation of complex A, but not complex B, when the labeled P-selectin GATA oligonucleotide was incubated with nuclear extracts from HEL and BAEC. Furthermore, the labeled mutant probe formed complex A, but not complex B. These data indicate that the core GATA sequence is required for formation of complex B, but not complex A.

To confirm that the consensus GATA element in the P-selectin promoter bound to a member of the GATA protein family, gel shift assays were performed with extracts from COS-7 cells transfected with an expression plasmid encoding human GATA-2. Labeled P-selectin probe was incubated with extracts from mock-transfected COS-7 cells (mock) or with COS-7 cells transfected with an expression plasmid encoding human GATA-2 (hGATA-2) in the present or absence of unlabeled P-selectin GATA, unlabeled human endothelin-1 GATA, or nonconsensus GATA oligonucleotides as competitors.

The hGATA-2-transfected COS-7 extracts, but not those from mock-transfected cells, formed a DNA-protein complex with the $^{32}$P-labeled P-selectin GATA probe. Formation of this complex was inhibited by addition of the unlabeled endothelin-1 GATA oligonucleotide as well as by the unlabeled P-selectin probe. These results indicate that the P-selectin GATA probe binds a member(s) of the GATA protein family.

Other Nuclear Protein Binding Sites.

The luciferase expression studies described above indicated that the sequences responsible for most of the P-selectin promoter activity in endothelial cells are located in the sequence between nt 4615 and 4851 of SEQ ID NO. 5 and that at least three positive regulatory sequences are located between nt 4615 and 4764 of SEQ ID NO. 5. In addition to these sites, gel shift studies also indicated the existence of at least three regulatory sites in a 52 base pair portion of the 5' flanking region of the P-selectin gene having the sequence from nt 4615 to 4666 of SEQ ID NO. 5. This conclusion was obtained by gel shift studies of four complexes that were first observed to form between nuclear protein extracts from several cell types and a double-stranded $^{32}$P-labeled oligonucleotide corresponding to the sequence from nt 4632 to 4672 of SEQ ID NO. 5. Starting with the complex with slowest mobility in the gels, these complexes were designated as I, then a closely-spaced doublet IIa and IIb, then III. Extracts from some cell types formed some, but not all, of the complexes. For example, complex I was not formed by extracts of HUVECs.

Complex I was also formed by mixing nuclear extracts with an oligonucleotide having the sequence of nt 4650 to 4669 of SEQ ID NO. 5. This sequence is not related to those of known DNA regulatory elements. Complex I was formed with nuclear extracts from BAECs, but complex formation was prevented when extracts were prepared from the same cells following stimulation with phorbol myristate acetate. These results indicate that the sequence of nt 4650 to 4669 of SEQ ID NO. 5 is bound by previously undescribed regulatory protein(s).

The complexes corresponding to the IIa and IIb doublet (referred to collectively as complex II for simplicity) represent interactions of the DNA with members of the NFκB family, a group of homodimeric or heterodimeric DNA-binding proteins that help regulate expression of many genes (Blank et al., *Trends Biochem. Sci.*, 17, pp. 135–140 (1992). Complex II was formed not only when nuclear extracts were mixed with the oligonucleotide having the sequence of nt 4632 to 4672 of SEQ ID NO. 5, but also when mixed with a oligonucleotide having the shorter sequence of nt 4642 to 4664 of SEQ ID NO. 5. Formation of complex II was inhibited by an unlabeled oligonucleotide having the sequence CGGCTGGGGATTCCCCATCT (SEQ ID NO. 11), which contains the NFκB element of the mouse H-2K$^b$ class I major histocompatibility (MHC) promoter. Complex formation was also inhibited by a combination of antisera to NFKB1 and NFKB2 subunits, two of the subunits found in certain dimeric NF-KB proteins, but not by preimmune sera. Furthermore, the labeled oligonucleotides bound to purified recombinant homodimers of NFKB1 and NFKB2, but not to homodimers of recombinant Rel A, another subunit found in some dimeric NF-KB proteins, or to heterodimers that contain the Rel A subunit in cell extracts. Methylation interference studies indicated that the GGGG sequence in the sense strand (nt 4646 to 4650 of SEQ ID NO. 5) and the GGGG in the antisense strand (nt 4654 to 4657 of SEQ ID No. 5) participated in direct contacts with NFKB1 and NFKB2 homodimers. Furthermore, a mutant oligonucleotide spanning the 4642 to 4664 sequence, in which the CCCC sequence at 4654 to 4657 was altered to ATAG, failed to interact with NFKB1 or NFKB2 in gel shift assays. These results indicate that the sequences recognized by NKFB1 and NFKB2 in the 4642 to 4664 region are consistent with known recognition features for members of the NF-κB family.

Formation of complex III required the inverted repeat sequence of nt 4635 to 4646 of SEQ ID NO. 5. Simultaneous mutations in both halves of the inverted repeat changing the sequence from CTTCCATGGAAG (nt 4635 to 4646 of SEQ ID NO. 5) to GTTGGTTCCAAG (SEQ ID No. 12), GTTG-GTTTTAAG (SEQ ID No. 13), or CTTCCATCCAAG (SEQ ID No. 14), abolished complex formation. An oligonucleotide having the sequence from nt 4626 to 4650 of SEQ ID NO. 5 also formed complex III. The sequence requirements for the formation of complex III indicate that one or more members of the ETS class of transcription factors may bind to this sequence of the 5' flanking region of the P-selectin gene. Complex III was formed by extracts from all cells tested (HEL, CHRF-288, K562, Jurkat, HL-60, HUVEC, BAEC, EAhy.926, and Hela), indicating that the transcription factor(s) interacting with sequence of 4626 to 4650 of SEQ ID No. 5 is widely expressed. Of the known ETS proteins, ets-2 and GABP are the most widely distributed (Macleod et al., *Trends Biochem. Sci.*, 17, pp 251–256 (1992)). However, oligonucleotides encoding known recognition sites for these proteins, i.e., TCGAGCAGGAAGT-GACGTCGA (SEQ ID NO. 15) or GGCCAAACCG-GAAGCATGTG (SEQ ID NO. 16) for ets-2 and AGCTTGCGGAACGGAAGCGGAAACCGCCGGATCG (SEQ ID NO. 17) for GABP, did not prevent formation of complex III with the labeled -238 to -214 oligonucleotide, indicating that ets-2 and GABP are not interacting with this region in the 5' flanking region of the P-selectin gene. These results indicate that the portion of the 5' flanking region of the P-selectin gene defined by nt 4635 to 4646 of SEQ ID NO. 5 is bound by previously undescribed protein(s). Such proteins may be unidentified members of the ETS family or of other families of transcription factors.

The gel-shift assays clearly indicate that sequences defined by nt 4650 to 4669, 4635 to 4646, and 4642 to 4664 of SEQ ID NO. 5, identify distinct domains within in the 5' flanking region of the P-selectin gene which play a significant role in the regulation of the expression of the P-selectin gene in endothelial and megakaryocytic cells. The gel-shift assays also indicate the existence of previously unknown regulatory proteins that bind these distinct domains of the 5' flanking region of the P-selectin gene. In particular, sequences defined by nt 4650 to 4669 and nt 4635 to 4646 of Seq ID No. 5 were sufficient to form two distinct complexes, i.e., complex I and complex III, respectively. Unlike the sequence defined by nt 4642 to 4664 of SEQ ID NO. 5, which has recognition features for proteins of the NFkB regulatory protein family, the sequences required for complex I have no obvious homology to sequences recognized by any known regulatory protein family. The sequences required to form complex III may allow binding of an unknown member of the ETS family or binding of a previously uncharacterized protein in some other class of transcription factors.

Accordingly, the sequences of the 5' flanking region of the P-selectin gene defined by nt 4650 to 4669 and 4635 to 4646 of SEQ ID NO. 5 are recognized and bound by regulatory proteins with previously undescribed features and are useful for the identification and isolation of such regulatory proteins. For example, such sequences could be attached to resins for use in the isolation of unknown DNA binding proteins by affinity chromatography. As another example, such sequences could be labeled using standard methodology and used to screen for clones expressing previously unknown regulatory proteins, or functional peptides thereof, in cDNA expression libraries made from mRNA from endothelial cells, megakaryocytic cells or other cells. Of course any other consecutive sequence of SEQ ID NO. 5 that has been shown to define a regulatory site in the 5' flanking region of the P-selectin gene could similarly be used in such methods to isolate the particular regulatory protein(s) that bind that sequence using techniques described herein.

IV. Diagnostic Methods

The luciferase expression studies, the gel shift studies, and the lacZ transgene experiments, above, clearly demonstrate that the integrity of the 5' flanking region of the P-selectin gene is critical for gene expression in endothelial and megakaryocytic cells. A disruption, deletion or other mutation in the sequence of nucleotides in this region can reduce or otherwise alter expression of the P-selectin gene, or heterologous gene properly ligated to this 5' flanking region. Accordingly, the DNA sequences of the 5' flanking region of the P-selectin gene can be used as hybridization probes to detect or screen for mutations in the 5' flanking region of the P-selectin gene of individuals with abnormal levels of expression of P-selectin, particularly those with elevated expression which have clinical symptoms of inflammation. In addition, DNA molecules including the DNA sequences of the 5' flanking region of the P-selectin gene can be transcribed to yield the corresponding RNA molecules, if in the judgment of the skilled practitioner it is more desirable to use RNA probes instead of DNA probes.

Calculations and empirical work by Lathe and others, Lathe, *J. Mol. Biol.*, 183, pp. 1–12 (1985); Ikuta et al., *Nucleic Acids Res.*, 15, pp. 797–811 (1987); and Sambrook et al., *Molecular Cloning, A Laboratory Manual, Second Edition*, pp. 11.7, 11.8 (Cold Spring Harbor Laboratory Press, Cold Spring Harbor, 1989), incorporated herein by reference, have established helpful guidelines for the skilled practitioner to select the length of probes most sensitive to mismatches in standard hybridization protocols. For example, to detect a single mismatch in a specific DNA sequence of the mammalian genome by hybridization, a probe length of 14 to 20 nucleotides is recommended (see e.g., Sambrook et al., pp. 11.7–11.8; Lathe, Table 6, p. 10). Accordingly, DNA and RNA molecules including DNA sequences, or the corresponding RNA sequences, which include at least 14 consecutive nucleotides of SEQ ID NO. 5, or functionally equivalent molecules, for example, obtained by hybridization under stringent conditions or substitution of specific bases followed by screening for function, for use as probes in diagnostic hybridization methods to detect mutations in the 5' flanking region of the P-selectin gene of individuals with altered (e.g., abnormally low or high) levels of expression of P-selectin. A whole series of nucleic acid probes including nucleotide sequences consisting essentially of 14 to 20 consecutive nucleotides of SEQ ID NO. 5 can be used to detect mutations along the entire or a portion of the 5' flanking region of the P-selectin gene.

Standard methods to isolate DNA and RNA from mammalian cells and tissues are well known in the art and can be used to prepare DNA (or RNA) for routine diagnostic screening by hybridization using the probes described herein. See, for examples of methods known to those skilled in the art which can be adapted for use herein using routine variation, Sambrook et al., *Molecular Cloning,* A Laboratory Manual, Second Edition, pp. 6.53–6.54 (DNA); pp. 7.6–7.11 (RNA) (Cold Spring Harbor Laboratory Press, Cold Spring Harbor, 1989); and Chomczyniski and Sacchi, *Anal. Biochem.,* 162, pp. 156–159 (1987) (RNA), the teachings of which are incorporated herein by reference. Furthermore, methods of carrying out hybridizations (e.g., Southern and Northern blot methods) of nucleic acids immobilized on various supports, such as nylon membranes or nitrocellulose filters, using DNA probes described herein labelled with some standard detectable marker, for example by using commercially available biotinylated, chemiluminescent, fluorescent, enzyme or radioactive labeling systems, are also routine and readily adapted to screening samples of DNA (or RNA) from individuals for alterations in the 5' flanking region of the P-selectin gene. See also, Leary et al., *Proc. Natl. Acad. Sci. USA,* 80, pp. 4045–4049 (1983) (biotinylated probes); and Sambrook et al., Chapter 9 ("Analysis of Genomic DNA by Southern Hybridization"), Chapter 10 ("Preparation of Radiolabeled DNA and RNA Probes")). In addition to using membranes, the advantages of probing nucleic acid samples immobilized to the plastic wells of microtiter plates has recently been advocated, offering another variation of the available methods of screening DNAs or RNAs by hybridization using nucleic acid probes (see Mitsuashi et al., *Nature,* 357, pp. 519–520 (1992). One of ordinary skill in the art is readily able to select from a variety of standard methods the particular conditions under which hybridizations are carried out in order to diagnostically screen DNA or RNA from individuals for alterations in the 5' flanking region of the P-selectin gene using the DNA molecules described herein as probes.

V. Therapeutic Methods and Compositions

As the above luciferase expression and the lacZ transgene expression studies indicate, nucleic acid molecules containing the 5' regulatory sequences of the P-selectin gene can be inserted into endothelial or megakaryocytic cells and used to regulate or inhibit heterologous gene expression in vivo. In the luciferase experiments, the plasmid pOLUC was used as the vector to carry and express the various recombinant 5' flanking region-luciferase gene constructs in endothelial cells. However, other vectors, including both plasmid and eukaryotic viral vectors, may be used to express a particular recombinant 5' flanking region-gene construct in endothelial or megakaryocytic cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, *Science*, 260, pp. 926–932 (1993); U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., *Science*, 261, pp. 209–211 (1993); incorporated herein by reference).

The 5' flanking sequences of the P-selectin gene can also be used to inhibit the expression of the P-selectin gene in cells and thereby affect the inflammatory response. For example, an antisense RNA of all or a portion of the 5' flanking region of the P-selectin gene can be used to inhibit expression of P-selectin in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat No. 4,980,286). Accordingly, DNA containing all or a portion of the sequence of the 5' flanking region of P-selectin gene can be inserted into an appropriate expression vector so that upon passage into the cell, the transcription of the inserted DNA yields an antisense RNA that is complementary to the mRNA transcript of the P-selectin gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the P-selectin gene to ensure that the antisense RNA contains complementary sequences present on the mRNA. Based on the transcriptional start site analysis (see above and FIG. 4) sequences between 4863 and 4842 of SEQ ID NO. 5 are most likely to be transcribed. Accordingly, the DNA to be inserted into the expression vector for antisense therapy should at least contain these sequences.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., *Proc. Natl. Acad. Sci. USA*, 75, pp. 280–284 (1978); Zamecnik et al., *PNAS*, 83, pp. 4143–4146 (1986); Wickstrom et al., *Proc. Natl. Acad. Sci. USA*, 85, pp. 1028–1032 (1988); Crooke, *FASEB J.*, 7, pp. 533–539 (1993). Furthermore, recent work has shown that improved inhibition of expression of a gene by antisense oligonucleotides is possible if the antisense oligonucleotides contain modified nucleotides (see, e.g., Offensperger et. al., *EMBO J.*, 12, pp. 1257–1262 (1993) (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., *Proc. Natl. Acad. Sci. USA*, 85, pp. 7079–7083 (1988) (synthesis of antisense oligonucleoside phosphoramidates and phosphorothioates to inhibit replication of human immunodeficiency virus-1); Sarin et al., *Proc. Natl. Acad. Sci. USA*, 85, pp. 7448–7794 (1989) (synthesis of antisense methylphosphonate oligonucleotides); Shaw et al., *Nucleic Acids Res*, 19, pp. 747–750 (1991) (synthesis of 3' exonuclease-resistant oligonucleotides containing 3' terminal phosphoroamidate modifications); incorporated herein by reference).

The sequences of the 5' flanking region of P-selectin can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., Maher et al., *Science*, 245, pp. 725–730 (1989); Orson et al., *Nucl. Acids Res.*, 19, pp. 3435–3441 (1991); Postal et al., *Proc. Natl. Acad. Sci. USA*, 88, pp. 8227–8231 (1991); Cooney et al., *Science*, 241, pp. 456–459 (1988); Young et al., *Proc. Natl. Acad. Sci. USA*, 88, pp. 10023–10026 (1991); Duval-Valentin et al., *Proc. Natl. Acad. Sci. USA*, 89, pp. 504–508 (1992); Blume et al., *Nucl. Acids Res.*, 20, pp. 1777–1784 (1992); Grigoriev et al., *J. Biol. Chem.*, 267, pp. 3389–3395 (1992).

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., *Mol. Cell. Biol.*, 8, pp. 963–973 (1988); Wickstrom et al., *Proc. Natl. Acad. Sci. USA*, 85, pp. 1028–1032 (1988)). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.*, 53, pp. 323–356 (1984) (phosphotriester and phosphite-triester methods); Narang et al., in *Methods Enzymol.*, 65, pp. 610–620 (1980) (phosphotriester method). Accordingly, DNA sequences of the 5' flanking region of the P-selectin gene described herein can be used to design and construct oligonucleotides including a DNA sequence consisting essentially of at least 15 consecutive nucleotides of SEQ ID NO. 5, with or without base modifications or intercalating agent derivatives, for use in forming triple helices specifically within the 5' flanking region of a P-selectin gene in order to inhibit expression of the gene in endothelial or megakaryocytic cells.

In addition, Rosenberg et al. (PCT WO 93/01286) teach the topical application of compositions including antisense oligonucleotides, generally 15–30 nucleotides in length, and Pluronic™ (polypropylene oxide—polyethylene oxide block copolymer) gel, which is liquid at 4° C. and solid at room temperature. Cells in direct contact with the gel compositions will take up the antisense oligonucleotides which will then base-pair to the complementary mRNA and inhibit expression of the target gene. Other biodegradable polymers can be substituted for the pluronics™ such as the polylactic acid and polyglycolic acid copolymers, polyethylene, and polyorthoesters which can be used to form implants for controlled release of the nucleic acid directly to a tissue where expression is desired.

Compositions including Pluronic™ gel and the antisense oligonucleotides or oligonucleotides complementary to one of the strands of the 5' flanking region (for triplex formation) can be delivered locally to the endothelial cells in blood vessels by using a catheter which is advanced into a vessel and applying the composition directly to the endothelial tissue. Other means of delivering such compositions locally to cells include using infusion pumps (e.g., from Alza Corporation, Palo Alto, Calif.) or incorporating the compositions into polymeric implants (see, e.g., P. Johnson and J. G. Lloyd-Jones, eds., *Drug Delivery Systems* (Chichester, England: Ellis Horwood Ltd., 1987), which can effect a sustained release of therapeutic compositions to the immediate area of the implant.

Inhibition of Inflammation by Inhibition of P-selectin Expression.

The above methods and compositions may be used locally or systemically to inhibit the expression of P-selectin in vivo and thereby inhibit inflammation. The ability to inhibit or otherwise regulate the inflammatory response at a site is desirable therapeutically because an inflammatory response may cause damage to the host if unchecked, since leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, and atherosclerosis. Systemic administration of compounds to achieve chronic systemic down-regulation of P-selectin expression may also be useful, for example, in a chronic disorder such as rheumatoid arthritis.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, indicating a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Modifications and variations of the present invention, will be recognized by those skilled in the art from the foregoing detailed description. It is understood that such modifications and variations are intended to come within the scope of this invention as defined in the specification, and that this invention is not limited by the specific embodiments that have been presented by way of example.

---

We claim:

1. A method for the expression of a gene in cultured endothelial cells or megakaryocytes comprising fusing the 5' end of the coding sequence of the gene to the 3' end of a DNA molecule comprising a nucleotide sequence consisting of nucleotides 1 to 4863 of SEQ ID NO. 5, or portions thereof effective to promote expression of a gene in cultured endothelial cells or megakaryocytes and consisting of at least 128 nucleotides immediately 5' from the translational start site of the P-selectin gene sequence including nucleotides 4736 to 4863 of SEQ ID NO. 5, to yield a recombinant gene construct;

inserting the recombinant gene construct into cultured endothelial cells or megakaryocytes and assaying for expression of the recombinant gene inserted into the cultured endothelial cells or megakaryocytes.

2. The method of claim 1 for the expression of a gene wherein the 5' end of the coding sequence of the gene is fused to the 3' end of a DNA molecule comprising a nucleotide sequence selected from the group consisting of nucleotides 1 to 4851, 3525 to 4851, 3525 to 4863, 3732 to 4866, 4163 to 4851, 4163 to 4863, 4206 to 4866, 4212 to 4866, 4405 to 4851, 4405 to 4863, 4457 to 4866, 4471 to 4866, 4505 to 4866, 4555 to 4666, 4555 to 4851, 4555 to 4863, 4615 to 4666, 4615 to 4764, 4615 to 4851, 4615 to 4861, 4615 to 4863, 4626 to 4650, 4632 to 4672, 4635 to 4646, 4641 to 4866, 4642 to 4664, 4645 to 4866, 4646 to 4657, 4650 to 4669, 4667 to 4863, 4667 to 4717, 4717 to 4863, 4727 to 4866, 4747 to 4757, 4734 to 4758, 4736 to 4764, 4761 to 4866 of SEQ ID NO. 5, and combinations thereof.

3. The method of claim 1 wherein the gene encodes P-selectin.

4. An isolated nucleic acid molecule comprising a nucleotide sequence consisting of nucleotides 1 to 4863 of SEQ ID NO. 5, or portions thereof including nucleotides 4736 to 4863 of SEQ ID NO. 5 fused to the 5' end of a gene.

5. The isolated nucleic acid molecule of claim 4 wherein the portions further comprise consecutive nucleotides of SEQ ID NO. 5 selected from the group consisting of nucleotides 1 to 4851, 3525 to 4851, 3525 to 4863, 3732 to 4866, 4163 to 4851, 4163 to 4863, 4206 to 4866, 4212 to 4866, 4405 to 4851, 4405 to 4863, 4457 to 4866, 4471 to 4866, 4505 to 4866, 4555 to 4666, 4555 to 4851, 4555 to 4863, 4615 to 4666, 4615 to 4764, 4615 to 4851, 4615 to 4861, 4615 to 4863, 4626 to 4650, 4632 to 4672, 4641 to 4866, 4642 to 4664, 4645 to 4866, 4646 to 4657, 4650 to 4669, 4667 to 4863, 4667 to 4717, 4717 to 4863, 4727 to 4866, 4734 to 4758, and 4761 to 4866 of SEQ ID NO. 5.

6. Cultured endothelial cells or megakaryocytes transfected with the DNA molecule of claim 4.

7. Cultured endothelial cells or megakaryocytes transfected with an expression vector comprising the DNA molecule of claim 4.

8. The endothelial cells or megakaryocytes of claim 6 wherein the DNA is stably incorporated into the genome of the cells.

9. An expression vector comprising the nucleic acid molecule of claim 4.

10. The expression vector of claim 9 wherein the vector is a retroviral vector.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single (D) TOPOLOGY: linear (ii) MOLECULE TYPE: DNA (synthetic)

(iii) HYPOTHETICAL: NO (iv) ANTI-SENSE: YES (ix) FEATURE:
    (A) NAME/KEY: misc_feature
    (B) LOCATION: 12
    (D) OTHER INFORMATION: /function="N is inosine."

(ix) FEATURE:
    (A) NAME/KEY: misc_feature
    (B) LOCATION: 15
    (D) OTHER INFORMATION: /function="The nucleotide at position 15 can also be A or C."

(ix) FEATURE:
    (A) NAME/KEY: misc_feature
    (B) LOCATION: 28
    (D) OTHER INFORMATION: /function="The nucleotide at position 28 can also be A, T, or C."

(x) PUBLICATION INFORMATION:
    (A) AUTHORS: Johnston, G. I.
                  Cook, R. G.
                  McEver, Rodger P.
    (C) JOURNAL: Abstract 1238 Supplement II Circulation
    (D) VOLUME: 78
    (F) PAGES: 4-
    (G) DATE: October-1988

(xi) SEQUENCE DESCRIPTION: SEQ ID NO:1:

GCTGTCCACT GNCCGAGGTT GTCACAGCGC ACAAT      35

(2) INFORMATION FOR SEQ ID NO:2:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (synthetic)

(iii) HYPOTHETICAL: NO (iv) ANTI-SENSE: YES (ix) FEATURE:
    (A) NAME/KEY: misc_feature
    (B) LOCATION: 12
    (D) OTHER INFORMATION: /function="N is inosine."

(ix) FEATURE:
    (A) NAME/KEY: misc_feature
    (B) LOCATION: 15
    (D) OTHER INFORMATION: /function="The nucleotide at position 15 can also be A or C."

(ix) FEATURE:
    (A) NAME/KEY: misc_feature
    (B) LOCATION: 28
    (D) OTHER INFORMATION: /function="The nucleotide at position 28 can also be C."

(xi) SEQUENCE DESCRIPTION: SEQ ID NO:2:

GCTGTCCACT GNCCGAGGTT GTCACATCTC ACAAT      35

(2) INFORMATION FOR SEQ ID NO:3:

(i) SEQUENCE CHARACTERISTICS:
    (A) LENGTH: 3142 base pairs
    (B) TYPE: nucleic acid (C) STRANDEDNESS: single
(D) TOPOLOGY: linear (i i) MOLECULE TYPE: cDNA (x i) SEQUENCE DESCRIPTION: SEQ ID NO:3:

```
TGGGCAGAAG GCAGAAAACC AGCAGAGTCA CAGAGGAGAT GGCCAACTGC CAAATAGCCA      60
TCTTGTACCA GAGATTCCAG AGAGTGGTCT TTGGAATTTC CCAACTCCTT TGCTTCAGTG     120
CCCTGATCTC TGAACTAACA AACCAGAAAG AAGTGGCAGC ATGGACTTAT CATTACAGCA     180
CAAAAGCATA CTCATGGAAT ATTTCCCGTA AATACTGCCA GAATCGCTAC ACAGACTTAG     240
TGGCCATCCA GAATAAAAAT GAAATTGATT ACCTCAATAA GGTCCTACCC TACTACAGCT     300
CCTACTACTG GATTGGGATC CGAAAGAACA ATAAGACATG GACATGGGTG GGAACCAAAA     360
AGGCTCTCAC CAACGAGGCT GAGAACTGGG CTGATAATGA ACCTAACAAC AAAAGGAACA     420
ACGAGGACTG CGTGGAGATA TACATCAAGA GTCCGTCAGC CCTGGCAAG TGGAATGATG      480
AGCACTGCTT GAAGAAAAAG CACGCATTGT GTTACACAGC CTCCTGCCAG GACATGTCCT     540
GCAGCAAACA AGGAGAGTGC CTCGAGACCA TCGGGAACTA CACCTGCTCC TGTTACCCTG     600
GATTCTATGG GCCAGAATGT GAATACGTGA GAGAGTGTGG AGAACTTGAG CTCCCTCAAC     660
ACGTGCTCAT GAACTGCAGC CACCCTCTGG GAAACTTCTC TTTTAACTCG CAGTGCAGCT     720
TCCACTGCAC TGACGGGTAC CAAGTAAATG GGCCCAGCAA GCTGGAATGC TTGGCTTCTG     780
GAATCTGGAC AAATAAGCCT CCACAGTGTT TAGCTGCCCA GTGCCCACCC CTGAAGATTC     840
CTGAACGAGG AAACATGATC TGCCTTCATT CTGCAAAAGC ATTCCAGCAT CAGTCTAGCT     900
GCAGCTTCAG TTGTGAAGAG GGATTTGCAT TAGTTGGACC GGAAGTGGTG CAATGCACAG     960
CCTCGGGGGT ATGGACAGCC CCAGCCCCAG TGTGTAAAGC TGTGCAGTGT CAGCACCTGG    1020
AAGCCCCCAG TGAAGGAACC ATGGACTGTG TTCATCCGCT CACTGCTTTT GCCTATGGCT    1080
CCAGCTGCAA ATTTGAGTGC CAGCCCGGCT ACAGAGTGAG GGGCTTGGAC ATGCTCCGCT    1140
GCATTGACTC TGGACACTGG TCTGCACCCT TGCCAACCTG TGAGGCTATT TCGTGTGAGC    1200
CGCTGGAGAG TCCTGTCCAC GGAAGCATGG ATTGCTCTCC ATCCTTGAGA GCGTTTCAGT    1260
ATGACACCAA CTGTAGCTTC CGCTGTGCTG AAGGTTTCAT GCTGAGAGGA GCCGATATAG    1320
TTCGGTGTGA TAACTTGGGA CAGTGGACAG CACCAGCCCC AGTCTGTCAA GCTTTGCAGT    1380
GCCAGGATCT CCCAGTTCCA AATGAGGCCC GGGTGAACTG CTCCCACCCC TTCGGTGCCT    1440
TTAGGTACCA GTCAGTCTGC AGCTTCACCT GCAATGAAGG CTTGCTCCTG GTGGGAGCAA    1500
GTGTGCTACA GTGCTTGGCT ACTGGAAACT GGAATTCTGT TCCTCCAGAA TGCCAAGCCA    1560
TTCCCTGCAC ACCTTTGCTA AGCCCTCAGA ATGGAACAAT GACCTGTGTT CAACCTCTTG    1620
GAAGTTCCAG TTATAAATCC ACATGTCAAT TCATCTGTGA CGAGGGATAT TCTTTGTCTG    1680
GACCAGAAAG ATTGGATTGT ACTCGATCGG GACGCTGGAC AGACTCCCCA CCAATGTGTG    1740
AAGCCATCAA GTGCCCAGAA CTCTTTGCCC CAGAGCAGGG CAGCCTGGAT TGTTCTGACA    1800
CTCGTGGAGA ATTCAATGTT GGCTCCACCT GTCATTTCTC TTGTAACAAT GGCTTTAAGC    1860
TGGAGGGGCC CAATAATGTG GAATGCACAA CTTCTGGAAG ATGGTCAGCT ACTCCACCAA    1920
CCTGCAAAGG CATAGCATCA CTTCCTACTC CAGGGTTGCA ATGTCCAGCC CTCACCACTC    1980
CTGGGCAGGG AACCATGTAC TGTAGGCATC ATCCGGGAAC CTTTGGTTTT AATACCACTT    2040
GTTACTTTGG CTGCAACGCT GGATTCACAC TCATAGGAGA CAGCACTCTC AGCTGCAGAC    2100
CTTCAGGACA ATGGACAGCA GTAACTCCAG CATGCAGAGC TGTGAAATGC TCAGAACTAC    2160
ATGTTAATAA GCCAATAGCG ATGAACTGCT CCAACCTCTG GGGAAACTTC AGTTATGGAT    2220
```

| | | | | | |
|---|---|---|---|---|---|
|CAATCTGCTC|TTTCCATTGT|CTAGAGGGCC|AGTTACTTAA|TGGCTCTGCA|CAAACAGCAT|2280|
|GCCAAGAGAA|TGGCCACTGG|TCAACTACCG|TGCCAACCTG|CCAAGCAGGA|CCATTGACTA|2340|
|TCCAGGAAGC|CCTGACTTAC|TTTGGTGGAG|CGGTGGCTTC|TACAATAGGT|CTGATAATGG|2400|
|GTGGGACGCT|CCTGGCTTTG|CTAAGAAAGC|GTTTCAGACA|AAAAGATGAT|GGGAAATGCC|2460|
|CCTTGAATCC|TCACAGCCAC|CTAGGAACAT|ATGGAGTTTT|TACAAACGCT|GCATTTGACC|2520|
|CGAGTCCTTA|AGGTTTCCAT|AAACACCCAT|GAATCAAAGA|CATGGAATTA|CCTTAGATTA|2580|
|GCTCTGGACC|AGCCTGTTGG|ACCCGCTCTG|GACCAACCCT|GTTTCCTGAG|TTTGGGATTG|2640|
|TGGTACAATC|TCAAATTCTC|AACCTACCAC|CCCTTCCTGT|CCCACCTCTT|CTCTTCCTGT|2700|
|AACACAAGCC|ACAGAAGCCA|GGAGCAAATG|TTTCTGCAGT|AGTCTCTGTG|CTTTGACTCA|2760|
|CCTGTTACTT|GAAATACCAG|TGAACCAAAG|AGACTGGAGC|ATCTGACTCA|CAAGAAGACC|2820|
|AGACTGTGGA|GAAATAAAAA|TACCTCTTTA|TTTTTTGATT|GAAGGAAGGT|TTTCTCCACT|2880|
|TTGTTGGAAA|GCAGGTGGCA|TCTCTAATTG|GAAGAAATTC|CTGTAGCATC|TTCTGGAGTC|2940|
|TCCAGTGGTT|GCTGTTGATG|AGGCCTCTTG|GACCTCTGCT|CTGAGGCTTC|AGAGAGTCC|3000|
|TCTGGATGGC|ACCAGAGGCT|GCAGAAGGCC|AAGAATCAAG|CTAGAAGGCC|ACATGTCACC|3060|
|GTGGACCTTC|CTGCCACCAG|TCACTGTCCC|TCAAATGACC|CAAAGACCAA|TATTCAAATG|3120|
|CGTAATTAAA|AGAATTTTCC|CC| | | |3142|

(2) INFORMATION FOR SEQ ID NO:4:

(i) SEQUENCE CHARACTERISTICS:
        (A) LENGTH: 830 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Ala Asn Cys Gln Ile Ala Ile Leu Tyr Gln Arg Phe Gln Arg Val
 1               5                   10                  15
Val Phe Gly Ile Ser Gln Leu Leu Cys Phe Ser Ala Leu Ile Ser Glu
                20                  25                  30
Leu Thr Asn Gln Lys Glu Val Ala Ala Trp Thr Tyr His Tyr Ser Thr
            35                  40                  45
Lys Ala Tyr Ser Trp Asn Ile Ser Arg Lys Tyr Cys Gln Asn Arg Tyr
        50                  55                  60
Thr Asp Leu Val Ala Ile Gln Asn Lys Asn Glu Ile Asp Tyr Leu Asn
 65                 70                  75                  80
Lys Val Leu Pro Tyr Tyr Ser Ser Tyr Tyr Trp Ile Gly Ile Arg Lys
                85                  90                  95
Asn Asn Lys Thr Trp Thr Trp Val Gly Thr Lys Lys Ala Leu Thr Asn
                100                 105                 110
Glu Ala Glu Asn Trp Ala Asp Asn Glu Pro Asn Asn Lys Arg Asn Asn
            115                 120                 125
Glu Asp Cys Val Glu Ile Tyr Ile Lys Ser Pro Ser Ala Pro Gly Lys
        130                 135                 140
Trp Asn Asp Glu His Cys Leu Lys Lys Lys His Ala Leu Cys Tyr Thr
145                 150                 155                 160
Ala Ser Cys Gln Asp Met Ser Cys Ser Lys Gln Gly Glu Cys Leu Glu
                165                 170                 175
Thr Ile Gly Asn Tyr Thr Cys Ser Cys Tyr Pro Gly Phe Tyr Gly Pro
```

-continued

```
                   180                        185                          190
Glu  Cys  Glu  Tyr  Val  Arg  Glu  Cys  Gly  Glu  Leu  Glu  Leu  Pro  Gln  His
          195                      200                      205

Val  Leu  Met  Asn  Cys  Ser  His  Pro  Leu  Gly  Asn  Phe  Ser  Phe  Asn  Ser
     210                      215                      220

Gln  Cys  Ser  Phe  His  Cys  Thr  Asp  Gly  Tyr  Gln  Val  Asn  Gly  Pro  Ser
225                      230                      235                      240

Lys  Leu  Glu  Cys  Leu  Ala  Ser  Gly  Ile  Trp  Thr  Asn  Lys  Pro  Pro  Gln
               245                      250                      255

Cys  Leu  Ala  Ala  Gln  Cys  Pro  Pro  Leu  Lys  Ile  Pro  Glu  Arg  Gly  Asn
               260                      265                      270

Met  Ile  Cys  Leu  His  Ser  Ala  Lys  Ala  Phe  Gln  His  Gln  Ser  Ser  Cys
          275                      280                      285

Ser  Phe  Ser  Cys  Glu  Glu  Gly  Phe  Ala  Leu  Val  Gly  Pro  Glu  Val  Val
     290                      295                      300

Gln  Cys  Thr  Ala  Ser  Gly  Val  Trp  Thr  Ala  Pro  Ala  Pro  Val  Cys  Lys
305                      310                      315                      320

Ala  Val  Gln  Cys  Gln  His  Leu  Glu  Ala  Pro  Ser  Glu  Gly  Thr  Met  Asp
               325                      330                      335

Cys  Val  His  Pro  Leu  Thr  Ala  Phe  Ala  Tyr  Gly  Ser  Ser  Cys  Lys  Phe
               340                      345                      350

Glu  Cys  Gln  Pro  Gly  Tyr  Arg  Val  Arg  Gly  Leu  Asp  Met  Leu  Arg  Cys
          355                      360                      365

Ile  Asp  Ser  Gly  His  Trp  Ser  Ala  Pro  Leu  Pro  Thr  Cys  Glu  Ala  Ile
     370                      375                      380

Ser  Cys  Glu  Pro  Leu  Glu  Ser  Pro  Val  His  Gly  Ser  Met  Asp  Cys  Ser
385                      390                      395                      400

Pro  Ser  Leu  Arg  Ala  Phe  Gln  Tyr  Asp  Thr  Asn  Cys  Ser  Phe  Arg  Cys
               405                      410                      415

Ala  Glu  Gly  Phe  Met  Leu  Arg  Gly  Ala  Asp  Ile  Val  Arg  Cys  Asp  Asn
               420                      425                      430

Leu  Gly  Gln  Trp  Thr  Ala  Pro  Ala  Pro  Val  Cys  Gln  Ala  Leu  Gln  Cys
          435                      440                      445

Gln  Asp  Leu  Pro  Val  Pro  Asn  Glu  Ala  Arg  Val  Asn  Cys  Ser  His  Pro
     450                      455                      460

Phe  Gly  Ala  Phe  Arg  Tyr  Gln  Ser  Val  Cys  Ser  Phe  Thr  Cys  Asn  Glu
465                      470                      475                      480

Gly  Leu  Leu  Leu  Val  Gly  Ala  Ser  Val  Leu  Gln  Cys  Leu  Ala  Thr  Gly
               485                      490                      495

Asn  Trp  Asn  Ser  Val  Pro  Pro  Glu  Cys  Gln  Ala  Ile  Pro  Cys  Thr  Pro
               500                      505                      510

Leu  Leu  Ser  Pro  Gln  Asn  Gly  Thr  Met  Thr  Cys  Val  Gln  Pro  Leu  Gly
          515                      520                      525

Ser  Ser  Ser  Tyr  Lys  Ser  Thr  Cys  Gln  Phe  Ile  Cys  Asp  Glu  Gly  Tyr
     530                      535                      540

Ser  Leu  Ser  Gly  Pro  Glu  Arg  Leu  Asp  Cys  Thr  Arg  Ser  Gly  Arg  Trp
545                      550                      555                      560

Thr  Asp  Ser  Pro  Pro  Met  Cys  Glu  Ala  Ile  Lys  Cys  Pro  Glu  Leu  Phe
               565                      570                      575

Ala  Pro  Glu  Gln  Gly  Ser  Leu  Asp  Cys  Ser  Asp  Thr  Arg  Gly  Glu  Phe
               580                      585                      590

Asn  Val  Gly  Ser  Thr  Cys  His  Phe  Ser  Cys  Asn  Asn  Gly  Phe  Lys  Leu
          595                      600                      605
```

| Glu | Gly | Pro | Asn | Asn | Val | Glu | Cys | Thr | Thr | Ser | Gly | Arg | Trp | Ser | Ala |
|---|---|---|---|---|---|---|---|---|---|---|---|---|---|---|---|
| | 610 | | | | 615 | | | | | 620 | | | | | |
| Thr | Pro | Pro | Thr | Cys | Lys | Gly | Ile | Ala | Ser | Leu | Pro | Thr | Pro | Gly | Leu |
| 625 | | | | | 630 | | | | | 635 | | | | | 640 |
| Gln | Cys | Pro | Ala | Leu | Thr | Thr | Pro | Gly | Gln | Gly | Thr | Met | Tyr | Cys | Arg |
| | | | | 645 | | | | | 650 | | | | | 655 | |
| His | His | Pro | Gly | Thr | Phe | Gly | Phe | Asn | Thr | Thr | Cys | Tyr | Phe | Gly | Cys |
| | | | 660 | | | | | 665 | | | | | 670 | | |
| Asn | Ala | Gly | Phe | Thr | Leu | Ile | Gly | Asp | Ser | Thr | Leu | Ser | Cys | Arg | Pro |
| | | 675 | | | | | 680 | | | | | 685 | | | |
| Ser | Gly | Gln | Trp | Thr | Ala | Val | Thr | Pro | Ala | Cys | Arg | Ala | Val | Lys | Cys |
| | 690 | | | | | 695 | | | | | 700 | | | | |
| Ser | Glu | Leu | His | Val | Asn | Lys | Pro | Ile | Ala | Met | Asn | Cys | Ser | Asn | Leu |
| 705 | | | | | 710 | | | | | 715 | | | | | 720 |
| Trp | Gly | Asn | Phe | Ser | Tyr | Gly | Ser | Ile | Cys | Ser | Phe | His | Cys | Leu | Glu |
| | | | | 725 | | | | | 730 | | | | | 735 | |
| Gly | Gln | Leu | Leu | Asn | Gly | Ser | Ala | Gln | Thr | Ala | Cys | Gln | Glu | Asn | Gly |
| | | | 740 | | | | | 745 | | | | | 750 | | |
| His | Trp | Ser | Thr | Thr | Val | Pro | Thr | Cys | Gln | Ala | Gly | Pro | Leu | Thr | Ile |
| | | 755 | | | | | 760 | | | | | 765 | | | |
| Gln | Glu | Ala | Leu | Thr | Tyr | Phe | Gly | Gly | Ala | Val | Ala | Ser | Thr | Ile | Gly |
| | 770 | | | | | 775 | | | | | 780 | | | | |
| Leu | Ile | Met | Gly | Gly | Thr | Leu | Leu | Ala | Leu | Leu | Arg | Lys | Arg | Phe | Arg |
| 785 | | | | | 790 | | | | | 795 | | | | | 800 |
| Gln | Lys | Asp | Asp | Gly | Lys | Cys | Pro | Leu | Asn | Pro | His | Ser | His | Leu | Gly |
| | | | | 805 | | | | | 810 | | | | | 815 | |
| Thr | Tyr | Gly | Val | Phe | Thr | Asn | Ala | Ala | Phe | Asp | Pro | Ser | Pro | | |
| | | | 820 | | | | | 825 | | | | | 830 | | |

( 2 ) INFORMATION FOR SEQ ID NO:5:

( i ) SEQUENCE CHARACTERISTICS:
        ( A ) LENGTH: 4866 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
AAGCTTCCTG TACCTGGAAT ATTAATATTT TATTTCAGAT TTGGGAAATT TTCAGCTAGC    60
AATCTTTAAA TATGCTTTCT GACCCCCTTT TCCTCTATTT TCTCCTTCTT AAACTACTGT   120
AATGTGAACA TTAGCTCTCT TTTTTAATTT TTAATTTAAT TTTTGTTTTT ATTTTTTGAG   180
ATGCAGTCTC ACTCTGTCAC CCAGGCTGGA GTGCAGTGGC ATGATCTCAG CTCACTGCAA   240
CCTTTGCCTT CTAGGTTGAA GAGATTCTGC TGCCTCAGTC TCCCCATGAG CTGGGATTAC   300
AGCATGTGCC ACAATCCCTG GCTAATTTTT TTGTATTTTT AGTAGAGACT GGGTTTCACC   360
ATGTTGGTCA GGCTGGTCTT GACTCCTGAC CTCAGGTGAT CCACTCACCT TGGCCTCCCA   420
AAGCGCTGGG ATTATGGCAT GAGCCACTGA GTCTGGCTGA ATGTTAGCTC TCTTGATGCT   480
GTCCCATAAA TCTTGTAGGC TTTCATCATT TCTTTTCATT CTTTTTCTC CTCTCACTGT    540
ATATTTTCAA AAACCTGTCT TCAGTTCACA GATTCTTTCT TCTGCTTGAT CAAGTCTGCT   600
ACTGGTGATT TCTACTGCAT TTCTCACTTC ATTCATTATA TTTTCAGCT CCAATTTCTT    660
TTATGATTTC AATCTTTCTG TTACATTTCT TATGTTGTGC ATTTATTGTT TCTCTGATTT   720
CACCAAATTG TTTCTCTGTG TTTGCTTCAA AGTAACTGAG CTTCTTTAAA AACAATTATC   780
```

```
TTGAATCCAT  TGTCAGGCCA  TTTGTAGTAC  TCCATTTCTT  TTGGGTCAGC  TACTGGGAAA   840
TTATTGTGTT  TCTTAGGTGG  TGATATTTTA  ATTTGGGTTT  TCATGTTTCT  TGCTGCCTTA   900
CACTGCTGTC  TGAGCATCTG  GTGGATCTGC  CCCAATTTCA  GGCTGTATGG  GCTGACTTTG   960
GTGGAGAAAT  ACCTTCTTAT  GTGGAATAAT  GCGAGGATGC  TGGCTGGGTG  GGATGCAAAA  1020
GTTCTGACTT  CAGTAGGGGC  AAAGCTGTGT  GGTCTCCATG  CAGATCTGTC  AGCTGAGGTT  1080
GGTGTTAGTG  AATACTACAG  GGATCCTTAG  AGGCCAACAC  TGTGGGTATC  TACAGTGGCA  1140
ATGAGGCTGT  TGAGGTTTTC  AATTGTGACA  AGTCCTCCAT  ATCTCTTTTT  TTCCCCACCT  1200
GGGAAGTCAT  GACTGAGGAC  ATCCCTCTTG  GAATTAGGTC  TAACTTGCAG  GCCTGCTCCT  1260
GGTGGTGGTG  ACACTGGTGT  CTGATGAACA  GTGCCCATGG  AGTGGCCAAG  AGCCAAGGCC  1320
TGAAGCATGG  GCATGCATGG  AGGGACCACA  GCACCAGATT  CAATTGTAGC  AATGGTACCA  1380
GTGCCCAAGG  CACAGGCATA  CTTACTATCA  CATTGATAAT  GGTGTGTAAA  ATGCAGGTAC  1440
TTATAAAGCA  GCTAAGGAGC  CAGGGACTTT  ACTGCATGCA  TACGCAGAGC  TACAGTGGCT  1500
CCAGGATCCA  GGGTGTGGGC  TAGCTCTCCT  TGGTGGCTGA  GCTGGTGACT  AGAGCATGGA  1560
CAGGCACAGA  GAAACCTTGA  CTCTAGGACC  CAGGGTGTTC  ACTAGCTCAC  TATAGTGGTG  1620
GCTCTGGTGT  TGGAGGTGTG  GGTGTGTGTA  GTACAGCCTC  AGAGACAGGG  TCTGGAGCGC  1680
AGGTGTGCAC  ATTACTACAG  CAGCTCTGGA  GTTGAGAATA  TGGGTTACCT  TTCTACAGTG  1740
GCTGAACTAG  TGTCTGGAGC  AAAGACTTTC  ACAGAGAGAA  CTTGGCTTGG  GGTCCCAGGG  1800
TGAGATCTAG  TTCACAACAG  CAGTGACTCC  AGTGTCTGAG  ACATGAGGAG  GTGCACTGCA  1860
GCCACAGAGC  CACAGTCCAG  AGTGTGAATA  TCTGTAGAGC  AGCCACAACT  TTTGGGGATC  1920
AGGAACACAC  ATAGAATTGT  GAGAGGTGGT  AACCCTGGCC  CCAGTCCTGG  CGAGTGCAAC  1980
AATAGCTGCT  TCTTGGTGAG  GGGGTGTGAG  GGGTAGTGCA  ACTGTGTTTC  CCTTTTTAGC  2040
ATCCTGCTAT  GGGAATGGCT  GTTGGACAAA  AGATGCCAGT  GTCCTCTGTG  GAGCAGGACA  2100
CTGGGGGCCT  CAGTGGCTCT  GTGTCACATG  ACTGACACAG  ATAGCCTACA  AATTTCTTTA  2160
TTCGTAGCTA  TCTCCTGGTG  TCTCATATAT  GCCAGTCTCA  CCGGTGATTC  TTCTACATGA  2220
ATATTCTTTC  TTTTCTCCAT  TGTGTTGTTC  CAAATTCTTT  AACAGGCTCT  TGAGCCCCAT  2280
CCCCCAACTC  CCCACCCTTG  TGAGGGCTAT  TTTGGTTTGT  GTATAACTGT  CTATGTTTGT  2340
TTTTTGTTG  GGGCATAAGG  CTGACATCTC  CTACTCCACC  ATCTTGCTAA  TGTCACCTGC  2400
ATAGGAATCT  TTTTATGCTT  TCCTTATATT  CACTAAAATT  TAACAATATC  AAACTTAAAA  2460
ACATATGATC  AATTGAACTT  ATTAATATCA  AACTTATTAT  AAATAAGAAA  CTACCAGGCT  2520
GGGCATGGTG  GCTCATGCCT  GTAATCCCAA  CATTTTGGGA  GGCTGAGGTG  AAAGGATCAC  2580
TTGAGCCCAG  GAATTCAAGA  CCAGCCTGGG  AAATATAGAG  AGACCCTATC  TCTAGAGATT  2640
TTTTTTTTTA  ATTAGCCAGT  AGTGATGGCA  CACATCTATA  GTCCCAGCTA  CTCAGGAGGC  2700
TGAGGTGGGA  GAATTGCTTG  AGCCCAGGAG  GTCAAGGCTG  CAGCAAGCAG  TAATCATGCC  2760
ACTGCACTCC  AGCCTGGGCC  GCAGAGTGAG  ACCCTGTCTC  AAAAAAAGAA  CCTACTAGTC  2820
TACATACCAC  ACTTCTTCAT  CCCCATCTGA  GACTATATAT  ATTTTTTCTA  ACATGAGGCA  2880
ATGCCAAAAA  GAGGAGCTGG  TGAGTGAAAG  TAAGAACAGA  AAGACATGGA  GGCAAGTCTT  2940
ATAGAATAAT  AGCCAACACT  TAAACTTACA  CTTAACAGCG  TGATAGGTAT  TGTTCCAAAC  3000
ACATTAAATT  CATTTAATGG  TCCTTACATG  TCTATGTATT  TGGTGATTAT  TATCCTTATT  3060
ATTCACATTG  CTGAGTGTAT  TATTCTGTTC  TCATGATGCT  GATAGAGACA  TACCCGAGAC  3120
TGGATAACTT  ATTAAAAAAA  AAAAGGTTTA  ATGGACTCAC  AGTTCCACGT  GGATGGGGAG  3180
```

-continued

| | | | | | | |
|---|---|---|---|---|---|---|
| TCCTCACAAT | CATGGTAGAA | AGCAAAAGAC | ACGTCTTACA | TGGCAGCAGG | GAAGAGAGAG | 3240 |
| AAATGAGAAC | CAAACAAAAG | GGGTTTCCCC | TTATAAAACC | ATCAGCTCTC | ATGCGACTTA | 3300 |
| TTCACTACCA | TGAGAACAGT | ATGGGGAAA | CCACCCCCAT | GATTCAATGA | TCTACCAGGT | 3360 |
| GCCTCCCACA | ACCTGTGGGA | ATTATGGGAG | CTACAATTCC | AGATGAGATT | TGGGTGGGGA | 3420 |
| CACAGCCAAA | CCACATCACT | GAGGAAACTG | AGTTATAGGG | AGATTAGTAA | CGCCCAACAC | 3480 |
| AGCTGGTAGG | TGGTGGAGCC | AGGCAGTCTG | ACTCTAGGGT | CTGGACTCTG | AACTGCATCA | 3540 |
| TGCTGCCAAG | AAGTTCCTCA | TTTTTTCCTC | TCTCAAGTT | TCCCTTATTC | CCCTACAGTC | 3600 |
| ATTCCTTCAA | CAGCATTTCC | TTCACCATCT | TTTCTACTTC | TACTATATAA | TTAATTTTTT | 3660 |
| CTTCTTGGTC | CCAAATTCCA | ACGTGCAAAT | GCAGCCTTAT | ATACCCTAAT | TCATCTTTAC | 3720 |
| CTTTAGACTT | TCTTCCAATG | TTTCTACTTC | ATTCCATTTT | AAATTTATCC | ATGAGATGCC | 3780 |
| TATTTACAAG | CTGTAACCAT | CATGAAGTGA | ATGAAGAATA | ATACCTACTA | CTGTACAATA | 3840 |
| GAATTCCAAG | AGTATAAATA | GGAGTTATGG | CTTTCTGACT | TGAAACTAAA | TACTTGATAC | 3900 |
| TTGATTTTGC | TGTCTGAGAT | CAATCTGAAA | AGTAATAATA | ATCACTAACA | TTTGTTGAGC | 3960 |
| ATCAATTGTG | GGCCAAGTGT | CATTTCAATC | ACTCTGTACA | TATTAACTCA | TTTCATCCTA | 4020 |
| CAACAACCCG | GTGAGGCAAG | TTCTGTTATT | CTGTTTTACA | GTTGAGGAAA | CAGAGGCATA | 4080 |
| GAGAGCTTAA | GTAGTTTGCC | CAGTAGATAG | CCAGAAGAGG | AGCCAGGATG | GGTCTCGGGC | 4140 |
| AGTTTAACAG | CACAGCTGAA | GTCTTAACCA | CTATGCCAAC | AGCTTTTGG | TCCTACACAT | 4200 |
| CCCATGGGAA | GAGGAAAATA | AAAAGGTATC | TATTTGTATA | CCTTTTTATT | TCTGATATAA | 4260 |
| GAAGCAGAAT | TCCTTTCACA | TGACCTATGT | CTATTAATA | CGTCATTTTG | AAACTTACCA | 4320 |
| ATAAAATTTC | CCAAGCGCCA | GAAAACTGTT | AGTGGCTTTT | TCCATTCTTC | TCTATTTTTT | 4380 |
| TTTGTGCTAC | TAATTTTGCT | TCTTTCCCTC | AGAAGGCTGC | CGGAATAGTA | AACATTCACT | 4440 |
| GACATGTCAT | AATTACTGGA | AAATGGGCAC | TGGAAAATCA | CATTGTAATT | AATTCAAAGC | 4500 |
| ATGTTTTCCA | AATGTACTAC | TTTAAATTGG | AGCTTATATC | ATAATCCAAG | GAAACCTTTG | 4560 |
| TGTGTGTACT | GTTCCCACAT | TGCTCAGCCT | GGGATATCCA | GGAGTAATTC | ACCTTGCGCC | 4620 |
| TGCCTCCAGA | CCATCTTCCA | TGGAAGGGGG | TGACCCCTTG | CCTCTTGGCA | ACCACTATTT | 4680 |
| CTAAGCTGCC | AACATTACTC | TTGCATTATC | AACATTCTAA | CTTCATGGGA | AGGGCTGTGG | 4740 |
| TGAGTTTCTG | GAATGTGAAT | AGGAAGTTGT | TTTTCTAAAC | AGCCTGACAC | TGAGGGGAGG | 4800 |
| CAGTGAGACT | GTAAGCAGTC | TGGGTTGGGC | AGAAGGCAGA | AAACCAGCAG | AGTCACAGAG | 4860 |
| GAGATG | | | | | | 4866 |

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TTCTGGTTTG TTAGTTCAGA GATCAGG        27

( 2 ) INFORMATION FOR SEQ ID NO:7:

( i ) SEQUENCE CHARACTERISTICS:
        ( A ) LENGTH: 25 base pairs
        ( B ) TYPE: nucleic acid

```
            ( C ) STRANDEDNESS: single
            ( D ) TOPOLOGY: linear ( i i ) MOLECULE TYPE: cDNA and DNA (synthetic)

( x i ) SEQUENCE DESCRIPTION: SEQ ID NO:7:

GATGTATATC TCCACGCAGT CCTCG                                                25
```

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

```
GAATTCGAGC TCGGTACCTT TTTTTTTTTT TTTTT                                     35
```

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA and DNA (synthetic)

( x i ) SEQUENCE DESCRIPTION: SEQ ID NO:9:

```
GAATTCGAGC TCGGTACC                                                        18
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA and DNA (synthetic)

( x i ) SEQUENCE DESCRIPTION: SEQ ID NO:10:

```
GTCGACTCTA GAATCAGCCC AGTTCTCAGC                                           30
```

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CGGCTGGGGA TTCCCCATCT                                                      20
```

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GTTGGTTCCA AG                                                                                                    12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GTTGGTTTTA AG                                                                                                    12

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CTTCCATCCA AG                                                                                                    12

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TCGAGCAGGA AGTGACGTCG A                                                                                          21

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GGCCAAACCG GAAGCATGTG                                                                                            20

( 2 ) INFORMATION FOR SEQ ID NO:17:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AGCTTGCGGA ACGGAAGCGG AAACCGCCGG ATCG                                                                            34